(12) United States Patent
Krichevsky

(10) Patent No.: US 9,284,569 B2
(45) Date of Patent: Mar. 15, 2016

(54) AUTOLUMINESCENT PHYTOSENSOR PLANTS AND USES THEREOF

(71) Applicant: Bioglow LLC, St. Louis, MO (US)

(72) Inventor: Alexander Krichevsky, St. Louis, MO (US)

(73) Assignee: Bioglow, LLC, St. Louis, MO (US)

( * ) Notice: Subject to any disclaimer, the term of this patent is extended or adjusted under 35 U.S.C. 154(b) by 295 days.

(21) Appl. No.: 13/894,043

(22) Filed: May 14, 2013

(65) Prior Publication Data

US 2014/0059722 A1    Feb. 27, 2014

Related U.S. Application Data

(60) Provisional application No. 61/647,323, filed on May 15, 2012.

(51) Int. Cl.
| | | |
|---|---|---|
| *C07K 14/435* | (2006.01) | |
| *C12N 15/82* | (2006.01) | |
| *A01H 1/00* | (2006.01) | |

(52) U.S. Cl.
CPC ........ *C12N 15/8214* (2013.01); *C12N 15/8201* (2013.01); *C12N 15/8209* (2013.01); *C12N 15/8212* (2013.01); *C12N 15/8243* (2013.01)

(58) Field of Classification Search
None
See application file for complete search history.

(56) References Cited

U.S. PATENT DOCUMENTS

| | | | | |
|---|---|---|---|---|
| 6,812,382 | B1 * | 11/2004 | Hitz et al. ............... | 800/295 |
| 7,129,391 | B1 * | 10/2006 | Daniell .................... | 800/278 |
| 2006/0057710 | A1 * | 3/2006 | Ishiura et al. .......... | 435/287.3 |
| 2010/0313303 | A1 | 12/2010 | Hudkins | |

FOREIGN PATENT DOCUMENTS

| | | | | |
|---|---|---|---|---|
| WO | WO 2009017821 A1 * | 2/2009 | ............ | C12N 15/82 |
| WO | 2011106001 A2 | 9/2011 | | |

OTHER PUBLICATIONS

Halanych (Hydrobiologia (2005) 535/536: 297-307).*
Bock et al, 2014, Curr. Opin. Biotechnol. 26:7-13.*
Wani et al, 2010, Current Genomics 11:500-512.*
Krichevsky et al. (PLoS ONE Nov. 2010, vol. 5, Issue 11, e15461).*
Zubko et al. (Transgenic Research 13: 523-530, 2004).*
Degraaf (Greenhouse Product News, Dec. 21, 2010).*
Bino (Theor Appl Genet (1985) 69:423-428).*
Zhou et al. (The Plant Journal (2007) 52, 961-972).*
Osteryoung et al. (The Plant Cell, vol. 10, 1991-2004, Dec. 1998).*
Madoka et al. Plant Cell Physiol. 43(12): 1518-1525 (2002).*
Krichevsky et al., "Autoluminescent Plants," PLoS One, vol. 5, Issue 11, Nov. 12, 2010, pp. 1-6.
Fei et al., "Identification of Plastid Intercistronic Expression Element (IEE) Facilitating the Expression of Stable Translatable Monocistronic mRNA's from Operons," The Plant Journal, vol. 52, Jul. 12, 2007, pp. 968-969.
International Search Report and Written Opinion, PCT Application No. PCT/US2013/040962 dated Oct. 11, 2013, 22 pgs.

* cited by examiner

*Primary Examiner* — Anne Kubelik
*Assistant Examiner* — Charles Logsdon
(74) *Attorney, Agent, or Firm* — Dennis A. Bennett

(57) ABSTRACT

Real-time monitoring of plant or environmental conditions is solved by Autoluminescent Phytosensor Plants (ALPS) disclosed herein that emit light in response to a specified stimulus or condition, which light emission is detected or measured by a sensor.

3 Claims, 10 Drawing Sheets

Figure 1:
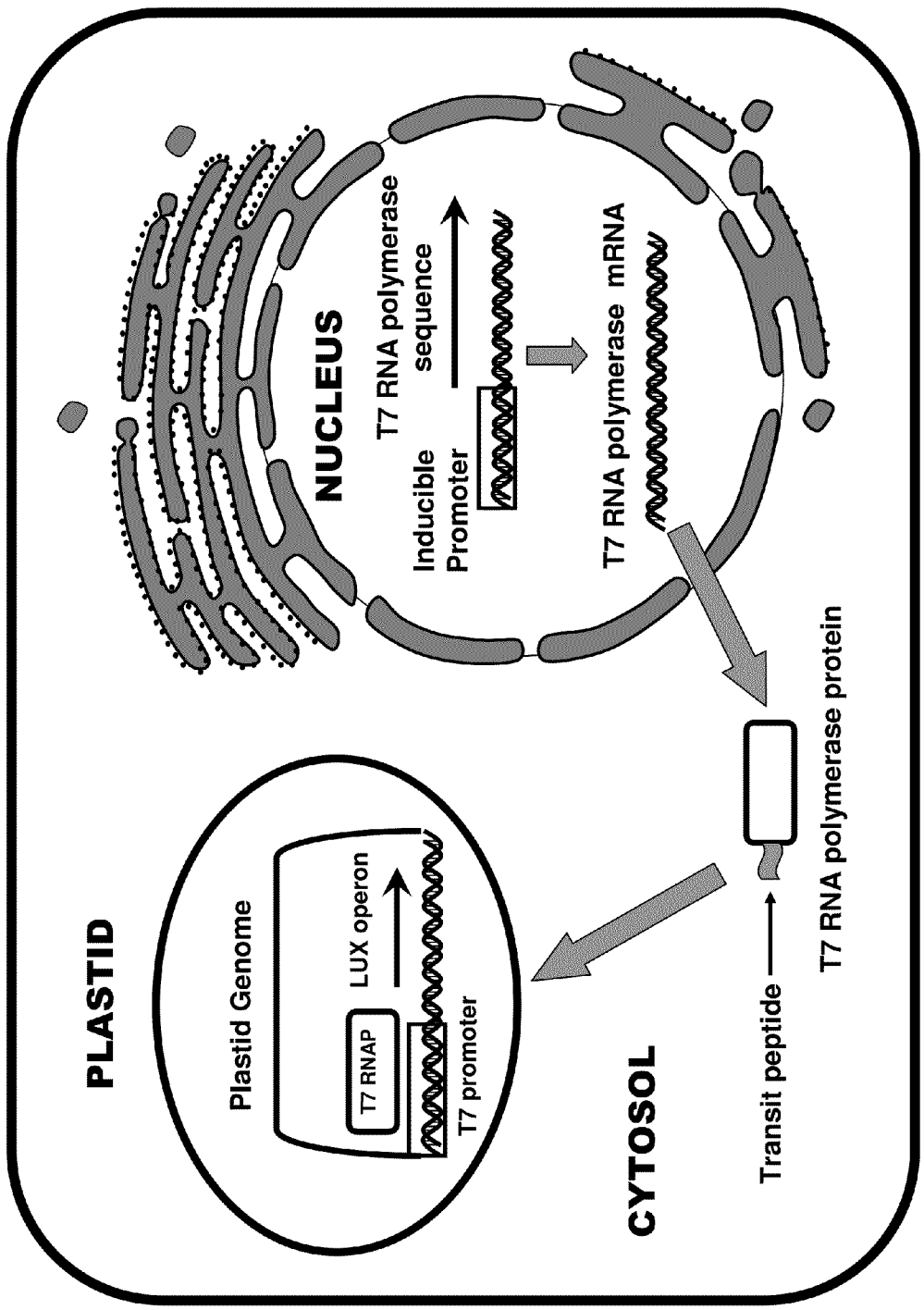

Transgenic *N. tabacum* made with pDI vector on the genetic background of transplastomic plant made using pBGL-T7p-LUX-tobacco

SEQUENCE LISTING

```
<160> NUMBER OF SEQ ID NOS: 31

<210> SEQ ID NO 1
<211> LENGTH: 50
<212> TYPE: DNA
<213> ORGANISM: UNKNOWN
<220> FEATURE:
<223> OTHER INFORMATION: PLASTIDAL IEE ELEMENT

<400> SEQUENCE: 1
taggatcgtt tatttacaac ggaatggtat acaaagtcaa cagatctcaa        50
```

```
<210> SEQ ID NO 2
<211> LENGTH: 1539
<212> TYPE: DNA
<213> ORGANISM: UNKNOWN
<220> FEATURE:
<223> OTHER INFORMATION: ACETYL-COACARBOXYLASE (ACCASE) SUBUNIT (ACCD)

<400> SEQUENCE: 2
atgactattc atctattgta ttttcatgca aatagggggc aagaaaactc tatggaaaga      60
tggtggttta attcgatgtt gtttaagaag gagttcgaac gcaggtgtgg gctaaataaa     120
tcaatgggca gtcttggtcc tattgaaaat accaatgaag atccaaatcg aaaagtgaaa     180
aacattcata gttggaggaa tcgtgacaat tctagttgca gtaatgttga ttatttattc     240
ggcgttaaag acattcggaa tttcatctct gatgacactt ttttagttag tgataggaat     300
ggagacagtt attccatcta ttttgatatt gaaaatcata tttttgagat tgacaacgat     360
cattcttttc tgagtgaact agaaagttct tttatagtt atcgaaactc gaattatcgg     420
aataatggat ttaggggcga agatccctac tataattctt acatgtatga tactcaatat     480
agttggaata atcacattaa tagttgcatt gatagttatc ttcagtctca aatctgtata     540
gatacttcca ttataagtgg tagtgagaat tacggtgaca gttacattta tagggccgtt     600
tgtggtggtg aaagtcgaaa tagtagtgaa acgagggtt ccagtagacg aactcgcacg     660
aagggcagtg atttaactat aagagaaagt tctaatgatc tcgaggtaac tcaaaaatac     720
aggcatttgt gggttcaatg cgaaaattgt tatggattaa attataagaa attttttgaaa     780
tcaaaaatga atatttgtga acaatgtgga tatcatttga aaatgagtag ttcagataga     840
attgaacttt tgatcgatcc gggtacttgg gatcctatgg atgaagacat ggtctctcta     900
gatcccattg aatttcattc ggaggaggag ccttataaag atcgtattga ttcttatcaa     960
agaaagacag gattaaccga ggctgttcaa acaggcatag gccaactaaa cggcattccc    1020
gtagcaattg gggttatgga ttttcagttt atggggggta gtatgggatc cgtagtcgga    1080
gagaaaatca cccgttttgat tgaatacgct gccaatcaaa ttttaccccct tattatagtg    1140
tgtgcttctg gggggcgcg catgcaggaa ggaagtttga gcttgatgca aatggctaaa    1200
atatcgtctg ctttatatga ttatcaatta aataaaaagt tattttatgt atcaatccttt    1260
acatctccga caactggtgg agtgacagct agttttggta tgttggggga tatcattatt    1320
gccgaaccca cgcctacat tgcatttgca ggtaaaagag taattgaaca aacattgaat    1380
aaaacagtac ccgaaggttc acaagcagct gaatacttat tccagaaggg tttattcgac    1440
ctaattgtac cacgtaatct tttaaaaagc gttctgagtg agttatttaa gctccacgcc    1500
tttttttcctt tgaatcaaaa gtcaagcaaa atcaagtag                           1539

<210> SEQ ID NO 3
<211> LENGTH: 3567
<212> TYPE: DNA
<213> ORGANISM: UNKNOWN
<220> FEATURE:
<223> OTHER INFORMATION: SECTION OF POINSETTIA CHLOROPLAST GENOME

<400> SEQUENCE: 3
ttcgggaacg cggacacagg tggtgcatgg ctgtcgtcag ctcgtgccgt aaggtgttgg      60
gttaagtccc gcaacgagcg caaccctcgt gtttagttgc cactgttgag tttggaaccc     120
tgagcagact gccggtgata agccggagga aggtgaggat gacgtcaagt catcatgccc     180
```

```
cttatgccct gggcgacaca cgtgctacaa tggccgggac aaagggtcgc gatcccgcga    240
gggtgagcta actccaaaaa cccgtcctca gttcggattt caggctgcaa ctcgcctgca    300
tgaagccgga atcgctagta atcgccggtc agccatacgg cggtgaattc gttcccgggc    360
cttgtacaca ccgcccgtca cactatggga gctggccatg cccgaagtcg ttaccttaac    420
cgcaaggagg gggatgccga aggcagggct agtgactgga gtgaagtcgt aacaaggtag    480
ccgtactgga aggtgcggct ggatcacctc cttttcaggg agaggtaatg cttgttgggt    540
attttggttt gacactgctt cacacccaaa aagaagggag ctacgtatga gttcaacttg    600
tcgacggaag tcttctttct cgacggtgaa gtaagaccaa gctcatgagc ttattatcct    660
aggtcggaac aagttgatag gatccccttt tttacgtccc catggccctt ccgcgtggcg    720
acatgggggc gaaaaaagga aagagaggga tgaggtttct ctcgcttttg gcatagcggg    780
ccccggcgg gaggcccgca cgacgggcta ttagctcagt ggtagagcgc gcccctgata    840
attgcgtcgt tgtgcctgga ctgtgagggc tctcagccac atggatagtt caatgtgctc    900
atcagcgcct gaccctgaga tgtggatcat ccaaggcaca ttagcatggc gtacttctcc    960
tgttcgaacc ggggtttgaa accaaacttc tcctcaggag gatagatggg gcgattcagg   1020
tgagatccaa tgtagatcca actttctatt cactcgtggg atccgggagg tccggggggg   1080
accaccatgg ctcctctctt ctcgagaatc catacatccc ttatcaatgt atggacagct   1140
atctctcgag cacaggttta ggttcggctt caatgggaaa ataaaatgga gcacctaaca   1200
acgtatcttc acagaccaag aactacgaga tcgccccttt cattctgggg cgacggaggg   1260
atcataacat tcgagccatt tttttcatgc ttttccggga ggtctggaga aagctgcaat   1320
caataggatt ttccgaaccc tcccttcgcg aaaggaagga ggtgaaattc ttttttccttt   1380
ccgcaggat caggagattg gatctagccg taagaagaat gcttggttga taaataactc   1440
acttcttggt cttcgacccc ctcagtcact acgaacgccc ccgatcagtg caatgggatg   1500
tgtctattta tctatctctt gactcgaaat gggagcaggt ttgaaaaagg atcttagagt   1560
gtctaaggtg gggccaggag ggtctcttaa cgccctcttc tttcttctca tcggagttat   1620
ttcaaaaata cttgccatgg taaggaagaa gggcagaaca agcacacttg gagagcgcag   1680
tacaacgagg aattgtatgc tgcgttcggg aaggatgaat cgctcccgaa aaggaatcta   1740
ttgattctct cccaattggt tggaccgtag gtgcgatgat ttacttcacg ggcgaggtct   1800
ctggttcaag tccaggatgg cccagctgcg ccaaagaaaa gaatagaaga agcatctgac   1860
tccttcgtcc acttggctcg gggggatata gctcagttgg tagagctccg ctcttgcaat   1920
tgggtcgttg cgattacggg ttggatgtct aattgtccag gcggtaatga tagtatcttg   1980
tacctgaacc ggtggctcac ttttttctaaa taatggggaa gaggaccgaa acatgccact   2040
gaaagactct actgagacaa agatgggctg tcaagaacgt agaggaggta agatgggcag   2100
ttggtcagat cgagtatgga tcgtacatgg acgatagttg gagtcagcgg ctctcctagg   2160
gttccctcat ctgggatccc tggggaagag gatcaagttg gcccttgcga acagcttgat   2220
gcactatctc ccttcaaccc tttagcgaaa tgcggcaaaa ggacggaaaa tccatggacc   2280
gaccccatcg tctccacccc gtaggaacta cgagatcacc ccaaggacgc cttcggcatc   2340
caggggtcgc ggaccgacca tagaaccctg ttcaataagt ggaacgcagt agctgtccgc   2400
tctcaggttg ggcagtaagg gtcggagaag ggcaatcact cattcttaaa accagcattc   2460
ttaagaccaa agagtgggcg gaaaggggg ctctccgttc ctggttttcc tgtagctgga   2520
tcctccggaa ccccaagaat ccttagttag aattagaata ggattccagc tcagcacctt   2580
```

```
ttgagatttt gagaagagtt gctctttgga gagcacagta cgatgaaagt tgtaagctgt   2640 gttcggggg  gagttattgt ctatcgttgg cctctatggt agaatcagtc ggggggcccga  2700 gaggcggtgg tttaccctgt ggcggatgtc agcggttcga gtccgcttat ctccaacttg   2760
tgaacttagc cggtacaaag ctatatgata gcacccaatt tttccgattc gtcagttcga   2820
tctatgattt ctcattcatg gacgttgata agatccttcc atttagcagc accttaggat   2880
ggcatagcct taaagttaag ggcgaggttc aaacgaggaa aggcttacgg tggatacccta  2940 ggcacccaga gacgaggaag ggcgtagtaa gcgacgaaat gcttcgggga gttgaaaata   3000
agcgtagatc cggagattcc cgaataggtc aacctttcaa actgctgctg aatccatggg   3060
caggcaagag acaacctggc gaactgaaac atcttagtaa ccagaggaaa agaaagcaaa   3120
agcgattccc gtagtagcgg cgagcgaaat gggagcagcc taaaccgtga aaacggggtt   3180
gtgggagagc aatacaagcg tcgtgctgct aggcgaagcg gtggagtgct gcaccctaga   3240
tggtgaaagt ccagtagccg aaagcattac tagcttacgc tctgacccaa gtagcatggg   3300
gcacgtggaa tcccgtgtga atcagcaagg accaccttgc aaggctaaat actcctgggt   3360
gaccgatagc gaagtagtac cgtgagggaa gggtgaaaag aaccccccatc ggggagtgaa   3420 atagaacatg aaaccgtaag ctcccaagca gtgggaggag cccggggctc tgaccgcgtg   3480
cctgttgaag aatgagccgg cgactcatag gcagtggctt ggttaaggga acccaccgga   3540
gccgtagcga aagcgagtct tcatagg                                      3567

<210> SEQ ID NO 4
<211> LENGTH: 3609
<212> TYPE: DNA
<213> ORGANISM: UNKNOWN
<220> FEATURE:
<223> OTHER INFORMATION: SECTION OF ROSE CHLOROPLAST GENOME
<220> FEATURE:
<221> NAME/KEY: misc_feature
<222> LOCATION: (1907)..(1907)
<223> OTHER INFORMATION: n is a, c, g, or t

<400> SEQUENCE: 4
ttcgggaacg cggacacagg tggtgcatgg ctgtcgtcag ctcgtgccgt aaggtgttgg    60
gttaagtccc gcaacgagcg caaccctcgt gtttagttgc caccgttgag tttggaaccc   120
tgagcagact gccggtgata agccggagga aggtgaggat gacgtcaagt catcatgccc   180
cttatgccct gggcgacaca cgtgctacaa tggccgggac aaagggtcgc gatcccgcga   240
gggtgagcta actccaaaaa cccgtcctca gttcggattg taggctgcaa ctcgcctaca   300
tgaagccgga atcgctagta atcgccggtc agccatacgg cggtgaattc gttcccgggc   360
cttgtacaca ccgcccgtca cactatggga gctggccatg cccgaagtcg ttaccttaac   420
cgcaaggggg gggatgccga aggcagggct agtgactgga gtgaagtcgt aacaaggtag   480
ccgtactgga aggtgcggct ggatcacctc cttttcaggg agagctaatg cttgttgggt   540
attttggttt gacactgctt cacacccaaa aagaagcgag ctacgtctga gttaaacttg   600
gaggtggaag tcttctttcg tttctcgacg gtgaagtaag actaagccca tgagcttatt   660
atcctaggtc ggaacaagtt gataggatcc cctttattta cgtccccatg tccctcccgt   720
gtggggacgt ggggggcgta aaaaggaaag agagggatgg ggtttctctc gcttttggca   780
tagcgggccc ccgcgggag  gcccgcacgg cgggctatta gctcagtggt agagcgcgcc   840
cctgataatt gcgtcgttgt gcctgggctg tgagggctct cagccacatg gatagttcaa   900
```

```
tgtgctcatc agcgcctgac cctgagatgt ggatcatcca aggcacatta gcatggcgta      960
cttctcctgt tcgaaccggg gtttgaaacc aaacctctcc tcaggaggat agatggggcg     1020
attcaggtga gatccaatgt agatccaact ttctattcac tcgtgggatc cgggcggtcc     1080
gggagggacc accacggctc ctctcttctc gagaatccat acatccctta tcagtatatg     1140
gacagctatc tctcgagcac aggtttaggt tcggcctcaa tgggaaaata aaacggagca     1200
cctaacaacg tatcttcaca gaccaagaac tacgagatcg ccctttcat tctggggtga     1260 cggagggatc gtaccattcg agccttttttt tttcatgctt tccccggagg tctggagaaa     1320
gctgcaatca ataggatttt cctaatcctc ccttcccgaa aggaagaacg tgaaattctt     1380
tttcctttcc gcagggacca ggagattgga tctagccgta agaagaatgt ttggctgata     1440
aataactcac ctcacttctt ggtcttcgac cccctcagtc actacgaacg cccccgatca     1500
gtgcaatggg atgtgtctat ttatctatct cttgactcga aatgggagca ggtttgaaaa     1560
aggatcttag agtgtctagg gttgggccag gagggtctct taacgccttc ttttttcttc     1620
tcatcggagt tatttcacaa agacttgcca tggtaaggaa gaagggagga acaagcacac     1680
ttggagagcg cagtacaacg gagagttgta tgctgcgttc gggaaggatg aatcgctccc     1740
gaaaaggaat ctattgattc tctcccaatt ggttggaccg taggtgcgat gatttacttc     1800
acgggcgagg tctctggttc aagtccagga tggcccagct gcgccaagga aagaatcga     1860 agaagcattt gactccttca tgcatgctcc acttggctcg ggggganata gctcagttgg     1920
tagagctccg ctcttgcaat tgggtcgttg cgattacggg ttggatgtct aattgtccag     1980
gcggtaatga tagtatcttg tacctgaacc ggtggctcac ttttttctaag taatggggaa     2040 gaggaccgaa acatgccact gaaagactct actgagacaa agatgggctg tcaagaacgt     2100
agaggaggta ggatgggcag ttggtcagat ctagtatgga tcgtacatgg acggtagttg     2160
gagtcggcgg ctctcctagg gttccctcat ctgggatccc tggggaagag gatcaagttg     2220
gcccttgcga acagcttgat gcactatctc ccttcaaccc tttgagcgaa atgcggcaaa     2280
aggaaaaaaa atccatggac cgaccccatc gtctccaccc cgtaggaact acgagatcac     2340
cccaaggacg cctttcggcat ccaggggtcg cggaccgacc atagaaccct gttcaataag     2400
cggaccgcat tagctgtccg cttttcaggtt gggcagtaag ggtcggagaa gggcaatcac     2460
tcattcttaa aaccagcatt cttaagacca aagagtcggg tgtaaaaggg gggaaagctc     2520
tccgttcctg gttctcctgt agctagatcc tccggaacca caagaatcct tagttagaat     2580
gggattccaa ctcagcacct ttcctttttt tttgagattt tgagaagagt tgctctttgg     2640
agagcacagt acgatgaaag ttgtaagctg tgttcggggg ggagttattg tctatcgtcg     2700
gcctctatgg tagaatcagt cggggggcctg agaggcggta gtttaccctg tggcggatgt     2760
cagcggttcg agtccgctta tctccaactc gcgaatttag cggatacaaa gctatatgat     2820
agcacccaat ttttccgatt cggcagttcg atctatgcta tgatttatca ttcatggacg     2880
ttgataagat ccttccatt agcagcacct tagggggatgg catagcctta aataaagtta     2940
agggcgaggt tcaaacgagg aaaggcttac ggtggatacc taggcaccca gagacgagga     3000
agggcgtagt aagcgacgaa atgcttcggg gagttgaaaa taagcgtaga tccgagatt      3060 cccgaatagg ttaacctttc gaactgctgc ttaatccatg ggcaggcaag agacaacctg     3120
gcgaactgaa acatcttagt agccagagga aaagaaagca aaagcgattc ccgtagtagc     3180
ggcgagcgaa atgggagcag cctaaaccgt gaaaacgggg ttgtgggaga gcaatacaag     3240
cgtcgtgctg ctaggcgaag cggtggagtg ctgcacccta gatggcgaga gtccagtagc     3300
```

```
cgaaagcatc actagcttac gctctgaccc gagtagcatg ggacacgtgg aatcccgtgt    3360
gaatcagcaa ggaccacctt gcaaggctaa atactcctgg gtgaccgata gtgaagtagt    3420
accgtgaggg aagggtgaaa agaaccccca tcggggagtg aaatagaaca tgaaaccgta    3480
agctcccaag cagtgggagg agcattgggc tctgaccgcg tgcctgttga agaatgagcc    3540
ggcgactcat aggcagtggc ttggttaagg gaacccaccg gagccgtagc gaaagcgagt    3600
cttcatagg                                                            3609

<210> SEQ ID NO 5
<211> LENGTH: 3236
<212> TYPE: DNA
<213> ORGANISM: UNKNOWN
<220> FEATURE:
<223> OTHER INFORMATION: SECTION OF PETUNIA CHLOROPLAST GENOME

<400> SEQUENCE: 5
cttcgggaac gcggacacag gtggtgcatg gctgtcgtca gctcgtgccg taaggtgttg      60
ggttaagtcc cgcaacgagc gcaaccctcg tgtttagttg ccatcgttga gtttggaacc     120
ctgaacagac tgccggtgat aagccggagg aaggtgagga tgacgtcaag tcatcatgcc     180
ccttatgccc tgggcgacac acgtgctaca atggccggga caaagggtcg cgatcccgcg     240
agggtgagct aaccccaaaa accgtcctca gttcggatt gcaggctgca actcgcctgc      300
atgaagccgg aatcgctagt aatcgccggt cagccatacg gcggtgaatt cgttcccggg     360
ccttgtacac accgcccgtc acactatggg agctggccat gcccgaagtc gttaccttaa     420
ccgcaaggag ggggatgccg aaggcagggc tagtgactgg agtgaagtcg taacaaggta     480
gccgtactgg aagtgcggc tggatcacct cctttcagg gagagctaat gcttgttggg       540
tattttggtt tgacactgct tcacaccccc aaaaaaaaag aagggagcta cgtctgagtt     600
aaacttggag atggaagtct tctttccttt ctcgacggtg aagtaagacc aagctcatga     660
gcttattatc ctaggtcgga acaagttgat aggacccct tttttacgtc cccatgttcc      720
ccccgtgtgg cgacatgggg gcgaaaaaag gaaagagagg gatggggttt ctctcgcttt     780
tggcatagcg ggcccccagt ggggaggctcg cacgacggg tattagctca gtggtagagc     840
gcgcccctga taattgcgtc gttgtgcctg ggctgtgagg gctctcagcc acatggatag     900
ttcaatgtgc tcatcggcgc ctgaccctga gatgtggatc atccaaggca cattagcatg     960
gcgtactcct cctgttcgaa ccggggtttg aaaccaaact cctcctcagg aggatagatg    1020
gggcgattca ggtgagatcc aatgtagatc caactttcga ttcactcgtg ggatccgggc    1080
ggtccggggg ggaccaccac ggctcctctc ttctcgagaa tccatacatc ccttatcagt    1140
gtatggacag ctatctctcg agcacaggtt taggttcggc ctcaatggga aaataaaatg    1200
gagcacctaa caacgcatct tcacagacca agaactacga gatcacccct ttcattctgg    1260
ggtgacggag ggatcgtacc attcgagccg tttttttctt gactcgaaat gggagcaggt    1320
ttgaaaaagg atcttagagt gtctagggtt gggccaggag ggtctcttaa cgccttcttt    1380
tttcttctca tcggagttat tttcacaaag acttgccagg gtaaggaaga aggggggaac    1440
aagcacactt ggagagcgca gtacaacgga gagttgtatg ctgcgttcgg gaaggatgaa    1500
tcgctcccga aaaggaatct attgattctc tcccaattgg ttggaccgta ggtgcgatga    1560
tttacttcac gggcgaggtc tctggttcaa gtccaggatg gccagctgc gccagggaaa     1620 agaatagaag aagcatctac tacttcatgc atgctccact tggctcgggg ggatatagct    1680
```

```
cagttggtag agctccgctc ttgcaattgg gtcgttgcga ttacggggttg gatgtctaat    1740 tgtccaggcg gtaatgatag tatcttgtac ctgaaccggt ggctcacttt ttctaagtaa    1800
tggggaagag gaccgaaacg tgccactgaa agactctact gagacaaaga tgggctgtca    1860
agaacgtaga ggaggtagga tgggcagttg gtcagatcta gtatggatcg tacatggacg    1920
gtagttggag tcggcggctc tcccagggtt ccctcatctg agatctctgg ggaagaggat    1980
caagttggcc cttgcgaaca gcttgatgca ctatctccct tcaacccttt gagcgaaatg    2040
cggcaaaaga aaaggaagga aaatccatgg accgacccca tcatctccac cccgtaggaa    2100
ctacgagatc accccaagga cgccttcggc atccaggggt cacggaccga ccatagaacc    2160
ctgttcaata agtggaacgc attagctgtc cgctctcagg ttgggcagtc agggtcggag    2220
aagggcaatg actcattctt attttgagtg agattttgag aagagttgct ctttggagag    2280
cacagtacga tgaaagttgt aagctgtgtt cgggggggag ttattgtcta tcgttggcct    2340
ctatggtaga atcagtcggg ggacctgaga ggcggtggtt taccctgcgg cggatgtcag    2400
cggttcgagt ccgcttatct ccaactcgtg aacttagccg atacaaagct ttatgatagc    2460
acccaatttt tccgattcgg cggttcgatc tatgatttat cattcatgga cgttgataag    2520
atccatccat ttagcagcac cttaggatgg catagcctta aaagtgaagg gcgaggttca    2580
aacgaggaaa ggcttacggt ggataccctag gcacccagag acgaggaagg gcgtagtaat    2640
cgacgaaatg cttcggggag ttgaaaataa gcatagatcc ggagattccc gaataggggca    2700 accttccgaa ctgctgctga atccatgggc aggcaagaga caacctggcg aactgaaaca    2760
tcttagtagc cagaggaaaa gaaagcaaaa gcgattcccg tagtagcggc gagcgaaatg    2820
ggagcagcct aaaccgtgaa aacggggttg tgggagagca atacaagcgt cgtgctgcta    2880
ggcgaagcag cctgaatgct gcaccctaga tggcgaaagt ccagtagccg aaagcatcac    2940
tagcttacgc tctgacccga gtagcatggg gcacgtggaa tcccgtgtga atcagcaagg    3000
accaccttgc aaggctaaat actcctgggt gaccgatagc gaagtagtac cgtgagggaa    3060
gggtgaaaag aacccccatc ggggagtgaa atagaacatg aaaccgtaag ctcccaagca    3120
gtgggaggag ccagggctct gaccgcgtgc ctgttgaaga atgagccggc gactcatagg    3180
cagtggcttg gttaagggaa cccaccggag ccgtagcgaa agcgagtctt catagg        3236
```

<210> SEQ ID NO 6
<211> LENGTH: 1065
<212> TYPE: DNA
<213> ORGANISM: Artificial Sequence
<220> FEATURE:
<223> OTHER INFORMATION: ARTIFICIAL LUX A NUCLEOTIDE SEQUENCE

<400> SEQUENCE: 6

```
atgaaaataa gtaatatttg tttctcatat caaccaccag gggagtccca tcaggaggtt     60
atggaaaggt ttatacgact aggtgtcgca tctgaagaat taaattttga tggattttat    120
actttagagc accattttac cgaatttgga ataactggta atttatatat tgcatgtgca    180
aacatactag gacgaactaa gcgtattcaa gttggcacaa tgggcatagt tcttcctaca    240
gagcatccgg ctcgacatgt agaatcacta cttgttcttg atcaattgtc taagggtaga    300
tttaattatg gaacggttag ggttttgtat cataaggatt ttcgagtgtt tgggacatcc    360
caggaggatt cccgaaaaac agcagaaaat ttctattcta tgattttaga tgcgtccaag    420 accgagtgt tgcatacgga cggggaggta gtagaatttc ctgatgtgaa tgtctaccca    480
gaagcctatt ctaaaaagca gcctacttgt atgactgcgg aatcttctga gactattact    540
```

-continued

```
tatttagcgg aaagagggct acctatggtg ttaagttgga ttatcccagt tagtgaaaaa      600
gtatctcaaa tggagttata taatgaagtg gccgctgaac atgggcatga tataaacaat      660
attgaacaca ttctaacatt tatttgctct gttaatgaag atggggagaa agccgatagt      720
gtatgtagga attttttgga gaattggtat gactcctaca agaatgccac aaacatcttt      780
aatgattcca accaaacaag aggttatgat tatttaaaag ctcaatggcg agagtgggtt      840
atgaaaggtt tagctgaccc acgaaggcgt cttgattatt ctaatgaatt aaatccggtc      900
ggtacacctg aacgttgtat cgaaattatt caaagtaata ttgatgcaac cgggataaaa      960
cacattaccg tgggctttga agctaatggt agtgaacagg aaattagaga atctatggaa     1020
ctttttatgg aaaaagttgc accgcatctt aaagatcccc aataa                     1065
```

<210> SEQ ID NO 7
<211> LENGTH: 981
<212> TYPE: DNA
<213> ORGANISM: Artificial Sequence
<220> FEATURE:
<223> OTHER INFORMATION: ARTIFICIAL LUX B NECLEOTIDE SEQUENCE

<400> SEQUENCE: 7

```
atgaactttg gattgttttt cctaaatttc caaccagaag gaatgacttc cgaaatggta       60
ctagataata tggttgatac agtagcattg gtagacaaag atgactatca tttcaagcgt      120
gtattggtgt ctgaacatca tttctccaaa atggcatta taggggagcc cttaaccgct      180
atatctttcc ttttaggtct aaccaagaga atagaaatag ttctttgaa tcaggttata      240 acgacccacc atcctgtaag aattggcgaa cagactggat tattagatca gatgtcttac      300
ggtcgtttcg ttttaggttt atcagattgc gttaatgatt tcgaaatgga tttttttaaa      360
cgaaaacgta gttcacaaca caacaattc gaagcatgtt atgaaatttt aaatgaagcc      420
ttaactacga attattgcca agcggatgat gattttttca attttccgag gatcagtgta      480
aatccccatt gtatctctga ggttaaacaa tacattttgg catcttctat gggtgtagtt      540
gaatgggccg ctcgaaaagg tcttcctta acgtatagat ggagtgatag tttagcagaa      600
aaagagaagt attatcagcg ttacttagcg gttgctaaag agaacaatat agatgtttca      660
aatatcgatc atcaatttcc tcttcttgta aatattaacg aaaatcgaag aatagcacga      720
gatgaagtac gtgagtacat tcagagttat gtatcagaag cctatcccac tgaccctaat      780
attgaacttc gtgtagaaga attgatcgaa caacacgcag tcgggaaagt cgatgaatat      840
tatgattcta cgatgcacgc tgtcaaagtt actggttcta aaaatttat tatatctttt      900 gaatctatga aaaataaaga tgacgtcact aaacttatca acatgttcaa ccaaaaaatc      960
aaggataact taataaagtg a                                                 981
```

<210> SEQ ID NO 8
<211> LENGTH: 1437
<212> TYPE: DNA
<213> ORGANISM: Artificial Sequence
<220> FEATURE:
<223> OTHER INFORMATION: ARTIFICIAL LUX C NUCLEOTIDE SEQUENCE,
      INCORPORATING ALA TO GLY MUTATION AT AMINO ACID POSITION 389

<400> SEQUENCE: 8

```
atgatcaaaa aaatccctat gataattggg ggagtagtcc agaacacatc cggttatgga       60
atgagagaat taacattaaa caataataaa gttaacattc aattatcac acaaagtgat      120 gtagaagcta ttcaatctct aaatattgag aacaaattga caataaatca gattgtaaat      180
```

-continued

```
ttcctttata ctgtaggcca aaaatggaaa tctgagacgt atagtcgtcg attaacttat    240
atcagagatt taatcaaatt cttaggttat agtcaggaaa tggctaaatt ggaagctaat    300
tggattagta tgatattatg ttctaaaagt gctttatatg acatagtaga aaatgattta    360
agtagtcgtc atatcattga tgaatggatt ccccaaggtg aatgctatgt aaaagcattg    420 cctaaggta  agtccgtaca cttgttagca ggaaatgttc ctttatcagg agtaacctcc    480
atactaagag caattcttac aaaaaatgaa tgcattatta aaactagttc agcagaccca    540
tttactgcca ctgcacttgt taactctttt atagacgttg atgccgaaca tcctataaca    600
cgatccatta gtgtaatgta ttggtcccat tctgaagatt tagcaattcc caaacaaata    660
atgtcttgtg ctgacgttgt tatagcatgg ggagggacg  atgcaataaa atgggcaact    720
gaacatgcac cttctcacgc agacatattg aaattcggac cgaaaaaatc catttccatt    780
gtcgataatc ctacggatat taaggcagct gctatcggag tggctcatga catttgtttt    840
tatgatcagc aagcatgctt ctcaacccaa gatatatatt atatcggaga ttcaattgat    900
attttctttg atgaattagc tcaacagtta aataaatata agacatttt  acctaaaggg    960 gaacgaaatt tcgatgagaa ggcagctttc tcccttactg aaagagagtg tcttttcgca    1020
aaatataaag ttcaaaaagg tgaatcccaa tcttggttgc ttacccaaag tccagcggga    1080
agttttggaa atcaaccttt gagtcgttct gcgtatattc atcaggtaaa tgatataagt    1140
gaagtaatac ccttcgtaca taaggagtt  actcaaactg tagctatcgc gccttgggaa    1200
tcaagtttta atacagaga  tatttttggct gagcatggtg ctgagcgtat cattgaagca    1260
ggaatgaata acattttcg  tgtaggaggt gcccacgatg ggatgcgacc cttgcaacgt    1320
ttggttaatt atatttctca tgaacgtcct agtacatata caacaaaaga tgttagtgta    1380
aaaatagaac agacaaggta tcttgaagaa gataaattct tagttttttgt accgtag      1437
```

<210> SEQ ID NO 9
<211> LENGTH: 948
<212> TYPE: DNA
<213> ORGANISM: Artificial Sequence
<220> FEATURE:
<223> OTHER INFORMATION: ARTIFICIAL LUX D NUCLEOTIDE SEQUENCE

<400> SEQUENCE: 9

```
atggaaaata cacaacatag tttacctatt gatcacgtaa tcgacatagg tgacaaccgt     60
tacatcaggg tgtgggaaac taaacctaaa aacaaagaaa ctaaagaaa  taataccata    120 gtgatagcgt ccggttttgc aagaagaatg gatcactttg ctggattagc tgaatatctt    180
gccaacaatg gattccgagt tattagatac gattcactaa atcatgtggg cttgtctagt    240
ggtgaaatta aacagtttag tatgtctgta ggtaaacatt ctttgctaac ggtaattgat    300
tggcttaaag aacgaaatat caacaatatt ggactaattg caagttcctt aagtgcccgt    360
atagcctatg aagtagccgc agaaattgat ttatccttcc ttataacagc agttggggtt    420
gtgaatttac gttctactct tgaaaagca  cttaaatatg attatttgca gatggaagtc    480
aatacgattc ctgaagactt aatatttgaa gggcataatc taggttcaaa agttttttgtg    540 actgattgtt ttgaaaacaa ctgggattct ttagactcaa ctattaataa atttgtgag     600 cttgatattc cgttcatagc tttcacttct gatggggatg attgggtttg tcaacatgaa    660 gtaaacacc  tagtgtccaa tgtaaaatct gacaaaaaaa agatatactc tttagttggt    720
agttcccatg atttggggga aaatttggtc gttttacgaa atttctatca aagtatgact    780
```

| aaagctgctg tctcattgga taggcaattg gttgaattag ttgatgaaat catagaacca | 840 |
| aattttgagg atttaaccgt aattacagtc aatgaaagaa gacttaaaaa taaaatagaa | 900 |
| aatgaaataa taaacagact agcagatcga gttcttgctt ccgtataa | 948 |

<210> SEQ ID NO 10
<211> LENGTH: 1122
<212> TYPE: DNA
<213> ORGANISM: Artificial Sequence
<220> FEATURE:
<223> OTHER INFORMATION: ARTIFICAL LUX E NUCLEOTIDE SEQUENCE,
      INCORPORATING GLN TO GLU MUTATION AT AMINO ACID POSITION 167

<400> SEQUENCE: 10

| atgtccacct tactaaacat cgatgcaacg gagattaaag ttagtaccga gatagatgat | 60 |
| ataatctttA caagtagtcc attaacttta ttatttgaag atcaagaaaa aattcagaaa | 120 |
| gaattaatac ttgaaagttt tcattatcat ataaccata ataaagatta caagtattat | 180 |
| tgtaatattc aggggttga tgagaacatt caatcaattg acgacattcc agtatttcct | 240 |
| acatccatgt ttaaatactc tcgtcttcat acagccgatg agagtaatat agaaaattgg | 300 |
| tttacatcat ccggtactaa aggcgttaag tctcatattg ctaggatag gcagtcaatt | 360 |
| gaaagattac taggatcagt taattatggt atgaaatatc ttggagaatt tcatgaacat | 420 |
| caacttgaac ttgtaaatat gggaccagat cgttttccg cttcaaacgt gtggttcaaa | 480 |
| tatgttatga gtttagtaga attgttatat cctactactt ttactgtgga aaatgatgag | 540 |
| atagattttg aacaaactat cttggcttta aaagcgatac aacgaaaagg aaaaggaata | 600 |
| tgtttaatag gaccgcctta ttttatatac ttgttatgcc attatatgaa agaacataat | 660 |
| atagaattta atgcagggc tcacatgttt attattacgg gaggggatg gaaaacaaaa | 720 |
| caaaagagg cgttaaatag gcaagattc aatcaacttc ttatggaaac attctcctta | 780 |
| tttcatgagt cacaaattag agacatattt aatcaagttg aattgaatac atgtttcttc | 840 |
| gaagattctc ttcaacgaaa acatgtgcca ccttgggtat atgctcgtgc attagatcct | 900 |
| gttactttga ctcccgtaga agacgggcag gaaggcttga tgtcttatat ggacgcctcc | 960 |
| agtacatcat atccgacttt catcgttacg gatgatattg gcattgtaag gcatctaaaa | 1020 |
| gagccagatc ccttccaagg tacaaccgta gaaattgtta gacgtcttaa cacacgagag | 1080 |
| caaaagggtt gttctttatc tatggctaca agtcttaaat aa | 1122 |

<210> SEQ ID NO 11
<211> LENGTH: 705
<212> TYPE: DNA
<213> ORGANISM: Artificial Sequence
<220> FEATURE:
<223> OTHER INFORMATION: ARTIFICIAL LUX G NUCLEOTIDE SEQUENCE

<400> SEQUENCE: 11

| atgatcttca actgtaaagt caaaaaagtt gaagcatccg attcacatat ttataaagtc | 60 |
| tttatcaaac ccgataagtg tttcgatttt aaagcaggcc aatatgttat tgtgtaccta | 120 |
| aacgggaaaa atttaccatt tagtatagcc aactgtccta catgtaatga attattggaa | 180 |
| ttacatgtag gcgggtctgt aaaagaatct gcaattgaag caatatcaca ctttattaat | 240 |
| gcttttatat atcaaaaaga atttactatt gatgctccgc atggagacgc tggttacga | 300 |
| gatgagtctc aatctccgct tttgttaata gctggcggca caggtttatc atatatcaat | 360 |
| agtatttaa gttgctgcat ttctaaacaa ctatcccaac cgatctattt atactggggt | 420 |

```
gtcaacaatt gtaaccttt  gtatgcagat caacaattaa aaactttggc cgcacaatat      480
cgtaatatta attatatccc tgtagttgag aatcttaata cagattggca aggaaaaatt      540
gggaatgtaa tagatgcagt aatcgaagat tttagtgacc tttcagattt cgacatctat      600
gtttgtggac ccttcggtat gtccagaaca gctaaagata ttctaatttc acaaaagaaa      660
gcaaacatag ggaagatgta ttcagatgct ttttcttaca cgtga                     705
```

<210> SEQ ID NO 12
<211> LENGTH: 702
<212> TYPE: DNA
<213> ORGANISM: Artificial Sequence
<220> FEATURE:
<223> OTHER INFORMATION: ARTIFICIAL E COLI FRE NUCLEOTIDE SEQUENCE

<400> SEQUENCE: 12

```
atgactactc tttcttgtaa ggtgacatca gtggaggcta taactgacac agtgtacaga       60
gttagaatcg taccagatgc agcatttagt tttagggccg gtcaatattt gatggttgta      120
atggacgaga gagataagag accattcagc atggcctcta ctccagatga aaagggtttt      180
atcgaactgc acattggagc atcagagatc aatttatacg caaaagcagt catggacagg      240
atcttaaagg accatcagat tgttgttgat attcctcacg cgaagcatg  gcttagggat      300 gatgaggaaa gacctatgat tctcatcgct ggcggaacag ggttctctta cgctaggtct      360
atactcctca ccgccctagc acgtaatcca aataggata  ttaccattta ctggggtggt      420
agagaagagc agcacccttta cgacctttgc gaattggagg cccttagctt aaagcatcct      480
ggtctacaag ttgtgccagt tgtcgaacaa cctgaggcag gatggagagg cgtacagga      540 acagtgctaa ctgccgttt  acaggatcat ggcactcttg ctgagcacga tatttatatt      600
gccggtagat tcgaaatggc taagattgca cgtgaccttt tttgttctga agaaatgcc       660 agggaagata gattgttcgg tgatgctttc gcattcattt ga                         702
```

<210> SEQ ID NO 13
<211> LENGTH: 585
<212> TYPE: DNA
<213> ORGANISM: Artificial Sequence
<220> FEATURE:
<223> OTHER INFORMATION: ARTIFICIAL V. FISCHERI YELLOW FLOURESCENT
      PROTEIN NUCLEOTIDE SEQUENCE

<400> SEQUENCE: 13

```
atgtttaaag gaattgtgga aggcattgga atcattgaga agatagacat atatacagac       60
cttgacaagt atgccatcag attccctgaa acatgttga  acggcattaa aaagagtct       120 tccattatgt ttaacggctg ctttcttaca gtgaccagcg ttaatagcaa catcgtctgg      180
tttgatattt tgagaagga  agctaggaaa ctggatacat ttagagaata taaggttgga      240
gatagagtca atttgggtac attcccaaag tttggtgctg catctggagg acatattttg      300
agtgcaagaa tatcttgcgt tgctagtatt attgagatta tagagaatga agattatcaa      360
cagatgtgga ttcagattcc tgagaacttt actgagttct taattgacaa agactatatt      420
gctgtcgatg gtatctcttt aacaatcgac actataaaaa acaatcagtt ttttattagt      480
ttgccgttaa aaatagctca aaataccaac atgaatgga  ggaaaaaggg agataaggtt      540
aacgtggagt tgtctaataa gattaacgct aatcagtgtt ggtga                     585
```

<210> SEQ ID NO 14
<211> LENGTH: 478
<212> TYPE: PRT

<213> ORGANISM: Photobacterium leiognathi

<400> SEQUENCE: 14

```
Met Ile Lys Lys Ile Pro Met Ile Ile Gly Val Val Gln Asn Thr
 1               5                  10                  15

Ser Gly Tyr Gly Met Arg Glu Leu Thr Leu Asn Asn Asn Lys Val Asn
            20                  25                  30

Ile Pro Ile Ile Thr Gln Ser Asp Val Glu Ala Ile Gln Ser Leu Asn
        35                  40                  45

Ile Glu Asn Lys Leu Thr Ile Asn Gln Ile Val Asn Phe Leu Tyr Thr
50                  55                  60

Val Gly Gln Lys Trp Lys Ser Glu Thr Tyr Ser Arg Arg Leu Thr Tyr
65                  70                  75                  80

Ile Arg Asp Leu Ile Lys Phe Leu Gly Tyr Ser Gln Glu Met Ala Lys
                85                  90                  95

Leu Glu Ala Asn Trp Ile Ser Met Ile Leu Cys Ser Lys Ser Ala Leu
            100                 105                 110

Tyr Asp Ile Val Glu Asn Asp Leu Ser Ser Arg His Ile Ile Asp Glu
        115                 120                 125

Trp Ile Pro Gln Gly Glu Cys Tyr Val Lys Ala Leu Pro Lys Gly Lys
130                 135                 140

Ser Val His Leu Leu Ala Gly Asn Val Pro Leu Ser Gly Val Thr Ser
145                 150                 155                 160

Ile Leu Arg Ala Ile Leu Thr Lys Asn Glu Cys Ile Ile Lys Thr Ser
                165                 170                 175

Ser Ala Asp Pro Phe Thr Ala Thr Ala Leu Val Asn Ser Phe Ile Asp
            180                 185                 190

Val Asp Ala Glu His Pro Ile Thr Arg Ser Ile Ser Val Met Tyr Trp
        195                 200                 205

Ser His Ser Glu Asp Leu Ala Ile Pro Lys Gln Ile Met Ser Cys Ala
210                 215                 220

Asp Val Val Ile Ala Trp Gly Gly Asp Asp Ala Ile Lys Trp Ala Thr
225                 230                 235                 240

Glu His Ala Pro Ser His Ala Asp Ile Leu Lys Phe Gly Pro Lys Lys
                245                 250                 255

Ser Ile Ser Ile Val Asp Asn Pro Thr Asp Ile Lys Ala Ala Ala Ile
            260                 265                 270

Gly Val Ala His Asp Ile Cys Phe Tyr Asp Gln Gln Ala Cys Phe Ser
        275                 280                 285

Thr Gln Asp Ile Tyr Tyr Ile Gly Asp Ser Ile Asp Ile Phe Phe Asp
290                 295                 300

Glu Leu Ala Gln Gln Leu Asn Lys Tyr Lys Asp Ile Leu Pro Lys Gly
305                 310                 315                 320

Glu Arg Asn Phe Asp Glu Lys Ala Ala Phe Ser Leu Thr Glu Arg Glu
                325                 330                 335

Cys Leu Phe Ala Lys Tyr Lys Val Gln Lys Gly Glu Ser Gln Ser Trp
            340                 345                 350

Leu Leu Thr Gln Ser Pro Ala Gly Ser Phe Gly Asn Gln Pro Leu Ser
        355                 360                 365

Arg Ser Ala Tyr Ile His Gln Val Asn Asp Ile Ser Glu Val Ile Pro
370                 375                 380

Phe Val His Lys Ala Val Thr Gln Thr Val Ala Ile Ala Pro Trp Glu
385                 390                 395                 400
```

```
                                    -continued

Ser Ser Phe Lys Tyr Arg Asp Ile Leu Ala Glu His Gly Ala Glu Arg
            405                 410                 415

Ile Ile Glu Ala Gly Met Asn Asn Ile Phe Arg Val Gly Gly Ala His
            420                 425                 430

Asp Gly Met Arg Pro Leu Gln Arg Leu Val Asn Tyr Ile Ser His Glu
            435                 440                 445

Arg Pro Ser Thr Tyr Thr Thr Lys Asp Val Ser Val Lys Ile Glu Gln
            450                 455                 460

Thr Arg Tyr Leu Glu Glu Asp Lys Phe Leu Val Phe Val Pro
465                 470                 475

<210> SEQ ID NO 15
<211> LENGTH: 373
<212> TYPE: PRT
<213> ORGANISM: Photobacterium leiognathi

<400> SEQUENCE: 15

Met Ser Thr Leu Leu Asn Ile Asp Ala Thr Glu Ile Lys Val Ser Thr
1               5                   10                  15

Glu Ile Asp Asp Ile Ile Phe Thr Ser Ser Pro Leu Thr Leu Leu Phe
            20                  25                  30

Glu Asp Gln Glu Lys Ile Gln Lys Glu Leu Ile Leu Glu Ser Phe His
            35                  40                  45

Tyr His Tyr Asn His Asn Lys Asp Tyr Lys Tyr Tyr Cys Asn Ile Gln
        50                  55                  60

Gly Val Asp Glu Asn Ile Gln Ser Ile Asp Asp Ile Pro Val Phe Pro
65                  70                  75                  80

Thr Ser Met Phe Lys Tyr Ser Arg Leu His Thr Ala Asp Glu Ser Asn
                85                  90                  95

Ile Glu Asn Trp Phe Thr Ser Ser Gly Thr Lys Gly Val Lys Ser His
            100                 105                 110

Ile Ala Arg Asp Arg Gln Ser Ile Glu Arg Leu Leu Gly Ser Val Asn
        115                 120                 125

Tyr Gly Met Lys Tyr Leu Gly Glu Phe His Glu His Gln Leu Glu Leu
130                 135                 140

Val Asn Met Gly Pro Asp Arg Phe Ser Ala Ser Asn Val Trp Phe Lys
145                 150                 155                 160

Tyr Val Met Ser Leu Val Gln Leu Leu Tyr Pro Thr Thr Phe Thr Val
                165                 170                 175

Glu Asn Asp Glu Ile Asp Phe Glu Gln Thr Ile Leu Ala Leu Lys Ala
            180                 185                 190

Ile Gln Arg Lys Gly Lys Gly Ile Cys Leu Ile Gly Pro Pro Tyr Phe
        195                 200                 205

Ile Tyr Leu Leu Cys His Tyr Met Lys Glu His Asn Ile Glu Phe Asn
210                 215                 220

Ala Gly Ala His Met Phe Ile Ile Thr Gly Gly Gly Trp Lys Thr Lys
225                 230                 235                 240

Gln Lys Glu Ala Leu Asn Arg Gln Asp Phe Asn Gln Leu Leu Met Glu
                245                 250                 255

Thr Phe Ser Leu Phe His Glu Ser Gln Ile Arg Asp Ile Phe Asn Gln
            260                 265                 270

Val Glu Leu Asn Thr Cys Phe Phe Glu Asp Ser Leu Gln Arg Lys His
        275                 280                 285

Val Pro Pro Trp Val Tyr Ala Arg Ala Leu Asp Pro Val Thr Leu Thr
290                 295                 300
```

```
Pro Val Glu Asp Gly Gln Glu Gly Leu Met Ser Tyr Met Asp Ala Ser
305                 310                 315                 320

Ser Thr Ser Tyr Pro Thr Phe Ile Val Thr Asp Asp Ile Gly Ile Val
            325                 330                 335

Arg His Leu Lys Glu Pro Asp Pro Phe Gln Gly Thr Thr Val Glu Ile
        340                 345                 350

Val Arg Arg Leu Asn Thr Arg Glu Gln Lys Gly Cys Ser Leu Ser Met
    355                 360                 365

Ala Thr Ser Leu Lys
    370

<210> SEQ ID NO 16
<211> LENGTH: 1437
<212> TYPE: DNA
<213> ORGANISM: Artificial Sequence
<220> FEATURE:
<223> OTHER INFORMATION: ARTIFICAL LUX C NUCLEOTIDE SEQUENCE WITHOUT ALA
      TO GLY MUTATION AT AMINO ACID POSITION 389

<400> SEQUENCE: 16
atgatcaaaa aaatccctat gataattggg ggagtagtcc agaacacatc cggttatgga      60
atgagagaat taacattaaa caataataaa gttaacattc caattatcac acaaagtgat     120
gtagaagcta ttcaatctct aaatattgag aacaaattga caataaatca gattgtaaat     180
ttcctttata ctgtaggcca aaaatggaaa tctgagacgt atagtcgtcg attaacttat     240
atcagagatt taatcaaatt cttaggttat agtcaggaaa tggctaaatt ggaagctaat     300
tggattagta tgatattatg ttctaaaagt gctttatatg acatagtaga aaatgattta     360
agtagtcgtc atatcattga tgaatggatt ccccaaggtg aatgctatgt aaaagcattg     420
cctaagggta agtccgtaca cttgttagca ggaaatgttc ctttatcagg agtaacctcc     480
atactaagag caattcttac aaaaaatgaa tgcattatta aaactagttc agcagaccca     540
tttactgcca ctgcacttgt taactctttt atagacgttg atgccgaaca tcctataaca     600
cgatccatta gtgtaatgta ttggtcccat tctgaagatt tagcaattcc caaacaaata     660
atgtcttgtg ctgacgttgt tatagcatgg ggaggggacg atgcaataaa atgggcaact     720
gaacatgcac cttctcacgc agacatattg aaattcggac cgaaaaaatc catttccatt     780
gtcgataatc ctacggatat taaggcagct gctatcggaa tggctcatga catttgtttt     840
tatgatcagc aagcatgctt ctcaaacccaa gatatatatt atatcggaga ttcaattgat     900
attttctttg atgaattagc tcaacagtta aataaatata aagacatttt acctaaaggg     960
gaacgaaatt tcgatgagaa ggcagctttc tcccttactg aaagagagtg tcttttcgca    1020
aaatataaag ttcaaaaagg tgaatcccaa tcttggttgc ttacccaaag tccagcggga    1080
agttttggaa atcaaccttt gagtcgttct gcgtatattc atcaggtaaa tgatataagt    1140
gaagtaaatac ccttcgtaca taaagcagtt actcaaactg tagctatcgc gccttgggaa    1200
tcaagttttta aatacagaga tattttggct gagcatggtg ctgagcgtat cattgaagca    1260
ggaatgaata acatttttcg tgtaggaggt gcccacgatg ggatgcgacc cttgcaacgt    1320
ttggttaatt atatttctca tgaacgtcct agtacatata caacaaaaga tgttagtgta    1380
aaaatagaac agacaaggta tcttgaagaa gataaattct tagttttttgt accgtag     1437

<210> SEQ ID NO 17
<211> LENGTH: 1122
<212> TYPE: DNA
```

<213> ORGANISM: Artificial Sequence
<220> FEATURE:
<223> OTHER INFORMATION: ARTIFICAL LUX E NUCLEOTIDE SEQUENCE WITHOUT GLN TO GLU MUTATION AT AMINO ACID POSITION 167

<400> SEQUENCE: 17

```
atgtccacct tactaaacat cgatgcaacg gagattaaag ttagtaccga gatagatgat      60
ataatcttta caagtagtcc attaacttta ttatttgaag atcaagaaaa aattcagaaa     120
gaattaatac ttgaaagttt tcattatcat tataaccata ataaagatta caagtattat     180
tgtaatattc aggggttga tgagaacatt caatcaattg acgacattcc agtatttcct     240
acatccatgt ttaaatactc tcgtcttcat acagccgatg agagtaatat agaaaattgg     300
tttacatcat ccggtactaa aggcgttaag tctcatattg ctagggatag gcagtcaatt     360
gaaagattac taggatcagt taattatggt atgaaatatc ttggagaatt tcatgaacat     420
caacttgaac ttgtaaatat gggaccagat cgttttccg cttcaaacgt gtggttcaaa      480
tatgttatga gtttagtaca attgttatat cctactactt ttactgtgga aaatgatgag     540
atagattttg aacaaactat cttggcttta aaagcgatac aacgaaaagg aaaaggaata     600
tgtttaatag gaccgcctta ttttatatac ttgttatgcc attatatgaa agaacataat     660
atagaattta atgcaggggc tcacatgttt attattacgg gaggggatg gaaaacaaaa      720
caaaagagg cgttaaatag gcaagatttc aatcaacttc ttatggaaac attctcctta     780
tttcatgagt cacaaattag agacatattt aatcaagttg aattgaatac atgtttcttc     840
gaagattctc ttcaacgaaa acatgtgcca ccttgggtat atgctcgtgc attagatcct     900
gttactttga ctcccgtaga agacgggcag gaaggcttga tgtcttatat ggacgcctcc     960
agtacatcat atccgacttt catcgttacg gatgatattg gcattgtaag gcatctaaaa    1020
gagccagatc ccttccaagg tacaaccgta gaaattgtta gacgtcttaa cacacgagag    1080
caaaagggtt gttcttatc tatggctaca agtcttaaat aa                        1122
```

<210> SEQ ID NO 18
<211> LENGTH: 31
<212> TYPE: DNA
<213> ORGANISM: Artificial Sequence
<220> FEATURE:
<223> OTHER INFORMATION: PCR primer

<400> SEQUENCE: 18

```
gcttccatgg gggaagcggt gatcgccgaa g                                     31
```

<210> SEQ ID NO 19
<211> LENGTH: 35
<212> TYPE: DNA
<213> ORGANISM: Artificial Sequence
<220> FEATURE:
<223> OTHER INFORMATION: PCR Primer

<400> SEQUENCE: 19

```
gtatgcatgc ttatttgccg actaccttgg tgatc                                 35
```

<210> SEQ ID NO 20
<211> LENGTH: 72
<212> TYPE: DNA
<213> ORGANISM: Artificial Sequence
<220> FEATURE:
<223> OTHER INFORMATION: PCR primer

<400> SEQUENCE: 20
tttccctcta gaaataattt tgtttaactt taagaaggag ataccatg ggggaagcgg    60 tgatcgccga ag                                                     72

<210> SEQ ID NO 21
<211> LENGTH: 60
<212> TYPE: DNA
<213> ORGANISM: Artificial Sequence
<220> FEATURE:
<223> OTHER INFORMATION: PCR primer

<400> SEQUENCE: 21
ccgttgtggt ctccctatag tgagtcgtat taatttcgcg gcgcgcctac cggtttaaac    60

<210> SEQ ID NO 22
<211> LENGTH: 30
<212> TYPE: DNA
<213> ORGANISM: Artificial Sequence
<220> FEATURE:
<223> OTHER INFORMATION: PCR primer

<400> SEQUENCE: 22
cagtcatatg atcctggcct agtctatagg                                    30

<210> SEQ ID NO 23
<211> LENGTH: 37
<212> TYPE: DNA
<213> ORGANISM: Artificial Sequence
<220> FEATURE:
<223> OTHER INFORMATION: PCR primer

<400> SEQUENCE: 23
ctgtctgcag tcgaatatag ctcttctttc ttatttc                            37

<210> SEQ ID NO 24
<211> LENGTH: 33
<212> TYPE: DNA
<213> ORGANISM: Artificial Sequence
<220> FEATURE:
<223> OTHER INFORMATION: PCR primer

<400> SEQUENCE: 24
caacgaattc ccaaaggaga ttacatgatt aag                                33

<210> SEQ ID NO 25
<211> LENGTH: 33
<212> TYPE: DNA
<213> ORGANISM: Artificial Sequence
<220> FEATURE:
<223> OTHER INFORMATION: PCR primer

<400> SEQUENCE: 25
cgttccgcgg ttacgtatag ctaaatgcat cag                                33

<210> SEQ ID NO 26
<211> LENGTH: 90
<212> TYPE: DNA
<213> ORGANISM: Artificial Sequence
<220> FEATURE:
<223> OTHER INFORMATION: PCR primer

<400> SEQUENCE: 26
gcaccgcgga gaccacaacg gtttccctct agaaataatt tgtttaact ttaagaagga    60 gatataccat gacaaccta agctgtaaag                                     90

```
<210> SEQ ID NO 27
<211> LENGTH: 38
<212> TYPE: DNA
<213> ORGANISM: Artificial Sequence
<220> FEATURE:
<223> OTHER INFORMATION: PCR primer

<400> SEQUENCE: 27
ctgtggtacc tcagataaat gcaaacgcat cgccaaac                              38

<210> SEQ ID NO 28
<211> LENGTH: 36
<212> TYPE: DNA
<213> ORGANISM: Artificial Sequence
<220> FEATURE:
<223> OTHER INFORMATION: PCR primer

<400> SEQUENCE: 28
cttcaagatc tccatggctt cctcagttct ttcctc                                36

<210> SEQ ID NO 29
<211> LENGTH: 33
<212> TYPE: DNA
<213> ORGANISM: Artificial Sequence
<220> FEATURE:
<223> OTHER INFORMATION: PCR primer

<400> SEQUENCE: 29
gtagggaatt cgcattgcac tcttccgccg ttg                                   33

<210> SEQ ID NO 30
<211> LENGTH: 34
<212> TYPE: DNA
<213> ORGANISM: Artificial Sequence
<220> FEATURE:
<223> OTHER INFORMATION: PCR primer

<400> SEQUENCE: 30
catcaggcgc gcctctatca tttaatctga gtcc                                  34

<210> SEQ ID NO 31
<211> LENGTH: 40
<212> TYPE: DNA
<213> ORGANISM: Artificial Sequence
<220> FEATURE:
<223> OTHER INFORMATION: PCR primer

<400> SEQUENCE: 31
ctgattccat ggtttccaaa gatttttttc tttccaatag                            40
```

AUTOLUMINESCENT PHYTOSENSOR PLANTS AND USES THEREOF

1.0 BACKGROUND OF THE INVENTION

1.1 Field of the Invention

Present invention relates to the field of biosensors.

1.2 Description of Related Art

Commercial agriculture depends on monitoring of various plant parameters, such as hydration, disease, ripeness, pest invasion, temperature, adequacy of nutrients, and other conditions to achieve successful yields. Since the beginning of agriculture, farmers relied primarily on their intuition and observation in assessing crop and field conditions. In recent decades, growers increasingly utilize various devices, including computerized systems, containing an assortment of sensing capabilities to more precisely follow plant, field, and greenhouse conditions (Wolf, B. (1996) *Diagnostic Technique for Improving Crop Production_1*, Haworth Press, pp. 185-187). These new developments are continuously leading to optimization of agricultural production through improved planting, water management, and other practices. However, while these new evolving approaches have substantially enhanced phytomonitoring, the existing methods are still cumbersome, imprecise, require complex and expensive equipment and, in many cases, do not provide real-time monitoring of a crop's condition.

An additional challenge of today's industrialized society is environmental contamination. Increasing effects of chemicals in the environment and their toxicity to human and animal health necessitate monitoring of pollutant levels. Common pollutants, among others, include heavy metals (cadmium, arsenic, mercury, etc), phenolic compounds, etc. Environmental analysis is typically carried out in by sampling of the suspected polluted area and later analyzing the samples using sophisticated methods, such as atomic absorption spectrometry, ion chromatography, etc. These are time consuming and expensive methods, which are not always available or feasible in practicality.

Therefore, there is a clear recognized need for an improved and robust phytosensing method capable of providing reliable real-time information.

U.S. Pat. No. 6,701,665 teaches monitoring of natural plant conditions using computerized systems; however, it does not disclose transgenic plants, nor does it contemplate measurement of active light emission or luminescence from plants.

US patent application 2005/0114923 suggests utilizing expression of plant pigments, such as anthocyanins, generally in response to contaminants. However, the application describes phenotypcial changes in plants, such as pigmentation, and does not relate to detecting plant autoluminescence or monitoring of light-emitting plants. The application also does not relate to or disclose genetic engineering of plastids, nor does it disclose computerized monitoring methods.

Patent applications PCT/US2008/009310, 60/953,337 and PCT/US10/25366 describe incorporation of luciferase and luciferin-related genes into plastids. PCT/US 10/25366 contemplates a genetic relay assay for induction of light emission. These documents do not, however, disclose the use of autoluminescent plants as phytosensors, or contemplate monitoring methods.

WO2007136432 contemplates bioluminescent plants containing LUX operon genes. However, it does not disclose the expression of the LUX operon from the plastid genome, nor does it provide suitable methods or vectors to integrate the LUX operon into plastidal genomes. Furthermore, it does not contemplate indirect luciferase pathway activation in plants (e.g., genetic relay assay as in PCT/US10/25366, etc.), thereby describing a different type of transgenic plants, as well as failing to provide for monitoring or survey methods. Similarly, U.S. Pat. No. 7,049,483 contemplates introduction of jellyfish luciferase and its substrate, coelenterazine, biosynthesis machinery into a plant to generate bioluminescent plants. However, it does not contemplate expression the jellyfish luciferase pathway from plastid genomes, does not provide for suitable methods or vectors to integrate these genes into plastidal genomes, and does not contemplate indirect luciferase pathway activation in plants. Finally, this reference does not contemplate the use of bioluminescent plants as phytosensors.

Therefore, a solid and robust system comprising an autoluminescent plant phytosensor and a computerized monitoring system is needed. The present invention provides for light emitting plants, having light emission machinery integrated within their plastidal genome, and a method of monitoring and surveying light emission thereof in order to utilize these plants as biosensors or phytosensors in agricultural and other settings.

The presently disclosed autoluminescent phytosensor (ALPS) plants, also referred as "ALPS plants" or simply as "ALPS", address this need by providing a simple, inexpensive, real-time monitoring alternative, superior to other biosensor systems. This technology can be widely used and find application in the monitoring of agricultural and horticultural crops, including ornamentals, and in environmental protection. Finally, ALPS can be used in basic plant research to monitor different plant parameters in real time and with high precision. Currently available monitoring systems frequently measure indirect parameters (e.g., $CO_2$ exchange rate (U.S. Pat. No. 6,701,665)), while ALPS produce signals directly in response to specific stimuli (dehydration, pest invasion, etc.). Moreover, while other reporter systems based on direct coupling of protein expression (e.g., GFP) in response to a given stimulus have been contemplated, those have been proven to be impractical. For example, GFP could not be detected using visualization approaches (see Kooshki et al (2003) "Pathogen inducible reporting in transgenic tobacco using a GFP construct", *Plant Science* 165:213-219). ALPS provide for practically feasible, real-time and direct response to very specific stimuli. The technology is non-destructive to plants, does not require any external substrates to be sprayed, and can be remotely sensed.

ALPS based on plastid-integrated light emission systems is a radically new concept. In the past, attempts to incorporate complex metabolic pathways into transgenic plants have been hampered by various limitations of genetic engineering technology. Creation of the world's first autoluminescent plant—a living plant organism capable of emitting visible light on its own, without the need for any external chemical or light sources—has been initially reported by us (Krichevsky et al. (2010) "Autoluminescent Plants", PLoS ONE 5(11): e15461). Here, for the first time, we describe the use of autoluminescent plants as phytosensors that can be used to monitor plant health, pathogen invasion, environmental contamination, and other conditions and stimuli affecting plant growth and development.

2.0 SUMMARY OF THE INVENTION

In one aspect, the present invention discloses the use of autoluminescent phytosensor plants (ALPS), containing genetically engineered plastids expressing a fully functional luciferase pathway and rendering the plants capable of emitting light. In ALPS, the luciferase pathway is activated as a result of a specific stimulus, such as drought, nutrient inadequacy, abnormal temperature, pollution, etc. Light emission commences when conditions present or induce such stimulus, and ceases when the stimulus ends.

In another embodiment, the present invention contemplates methods of monitoring ALPS. The monitoring methods involve the use of a luminescence sensor, preferably a photosensor, placed on, in proximity to, or remotely to a plant. The sensor-collected data are used to interpret and monitor environmental conditions or a plant's physiological state.

In yet another embodiment, the present invention contemplates a method for designing genetically engineered organisms, including but not limited to ALPS, with reduced regulatory requirements. Deregulation of transgenic plants for commercialization is an expensive and time-consuming matter, a process that may take several years and typically requires multimillion dollar investment per crop. Equivalent-in-traits transgenic plants can be engineered in many ways, and the provided method encompasses genetic design of a transgenic organism that will result in reduced regulatory burden as compared to a phenotypically equivalent transgenic organism.

Additional embodiments of the current invention describe methods to modify and enhance plant autoluminescence, utilize a variety of light emission systems from various organisms to generate autoluminescent plants, and to genetically transform specific varieties of plants.

More particularly, among its various aspects, the present invention includes the following:

1. An autoluminescentphytosensor (ALPS) plant monitoring system, comprising:
   (i) a plant containing a complete or partial LUX operon integrated within a plastidal genome thereof, wherein expression or activity of said operon is induced or complemented by a nucleus-integrated factor activated by an environmental or plant physiological condition;
   (i) at least one luminescence data detecting sensor positioned on, in proximity to, or remotely from said plant, wherein said sensor detects luminescence emitted from said plant;
   (ii) at least one transmitter that receives said luminescence data from said sensor; and
   (iii) a communication network that receives said luminescence data from said transmitter and conveys it to a receiver.
2. The autoluminescentphytosensor (ALPS) plant monitoring system of 1, wherein said plant is selected from the group consisting of an agronomic crop plant, a horticultural crop plant, and an ornamental plant.
3. The autoluminescentphytosensor (ALPS) plant monitoring system of 1 or 2, wherein said communication network is selected from the group consisting of a telephone network, a cellular telephone network, a computer network, a satellite network, and a combination of any of the foregoing.
4. The autoluminescentphytosensor (ALPS) plant monitoring system of any one of 1-3, wherein said environmental or plant physiological condition is selected from the group consisting of hydration, disease, pathogen or pest attack, pollution, nutrient deficiency, temperature, pollution, ripeness, radiation exposure, and senescence.
5. A transgenic plant cell containing a LUX operon comprising LUX genes integrated within a plastidal genome therein,
   wherein any or all of said LUX genes are separated by an intercistronic expression element (IEE) operably linked thereto, and
   wherein expression of said LUX genes is enhanced by a heterologous translational leader sequence operably linked to one or more of said LUX genes.
6. The transgenic plant cell of 5, wherein a heterologous translational leader sequence is linked to each of said LUX genes.
7. The transgenic plant cell of 5 or 6, wherein said heterologous translational leader sequence is selected from the group consisting of a T7g10 leader sequence, a canonical bacterial Shine-Dalgarno sequence AGGAGG, and an rbcL leader sequence.
8. An autoluminescent plant cell, containing plastids that have an altered size, an altered shape, and/or containing an altered number of plastids as compared to an otherwise identical cell containing wild-type plastids.
9. The autoluminescent plant cell of 8, wherein light emission by said autoluminescent plant cell is increased or decreased.
10. The autoluminescent plant cell of 9, wherein said increase or decrease is in a range selected from the group consisting of from about 0.1-fold to about 100-fold, from about 1-fold to about 50-fold, and from about 5-fold to about 25-fold.
11. The autoluminescent plant cell of any one of 8-10, wherein said alteration of plastid size, shape, and/or number of plastids is due to overexpression or suppression of chloroplast division genes.
12. A cell, in which a LUX operon and a protein exhibiting plastidal accD functionality are coexpressed, and wherein said accD is overexpressed.
13. The cell of 12, which is a bacterial cell or a plant cell.
14. The cell of 12 or 13, in which LUX operon light output is increased.
15. The cell of 14, wherein said increase in LUX operon light output is in the range of from about 0.1-fold to about 1000-fold.
16. A transgenic or transplastomic plant of *Petunia* cv. "Perfectunia Blue", *Nicotiana* Alata cv. "Whisper Rose Shades", or *Nicotiana Sylvestris* cv. "Only the Lonely".
17. A method of transforming a poinsettia plastid, comprising introducing into said plastid an expression cassette comprising at least one transgene of interest, wherein said expression cassette is flanked by sequences comprising about 100 to about 3,000 contiguous nucleotides of SEQ ID NO:3.
18. A method of transforming a rose plastid, comprising introducing into said plastid an expression cassette comprising at least one transgene of interest, wherein said expression cassette is flanked by sequences comprising about 100 to about 3,000 contiguous nucleotides of SEQ ID NO:4.
19. A method of transforming a *petunia* plastid, comprising introducing into said plastid an expression cassette comprising at least one transgene of interest, wherein said expression cassette is flanked by sequences comprising about 100 to about 3,000 contiguous nucleotides of SEQ ID NO:5.
20. A plastid transformation vector comprising an expression cassette,
   wherein said expression cassette comprises luciferase pathway genes arranged in the form of an operon driven by an operably linked, common promoter that drives expression of said luciferase pathway genes;

wherein at least one additional promoter is present and operably linked to at least one of said luciferase pathway genes within said operon, and which drives expression of at least one of said luciferase pathway genes;

wherein said expression cassette is present and functioning within a plastid of a plant cell; and wherein said plant cell is autoluminescent.

21. An autoluminescent plant expressing a functioning luciferase pathway, comprising luciferase and one or more luciferin biosynthesis genes integrated in a plastid genome, wherein said luciferase pathway is obtainable from Cnidaria (Coelenterates) or Ctenophores (e.g., *Aequorea Victoria, Periphylla periphylla*, or *Renilla reniformis*, or *Obelia* or *Mnemiopsis* species); orders of Coleoptera, Collembola, Hemiptera, Diptera (e.g., *Photinus pyralis*, or *Arachnocampa luminosa* or *Orfelia fultoni*); Dinoflagellata or Radiolaria (e.g., *Gonyaulax polyedra* or *Thalassicolla* species); Annelids (e.g., *Diplocardia longa, Chaetopterus variopedatus*, or *Odontosyllis* species); Mollusca (e.g., *Pholas dactylus, Watasenia scintillans*, or *Latia* species); Crustacea (e.g., *Vargula hilgendorfii, Cypridina hilgendorfii*, or *Meganyctiphanes norvegica*); Fungi (e.g., *Panellus stipticus* or *Mycena citricolor*); Echinodermata (e.g., *Ophiopsila californica*); or Diplopoda or Chilopoda (e.g., *Luminodesmus sequoiae* or *Orphaneus brevilabatus*).

22. The autoluminescent plant of 21, wherein said plastid is selected from the group consisting of a proplastid, an etioplast, a chloroplast, a chromoplast, an amyloplast, an elaioplast, a gerontoplast, a leucoplast, and a photoheterotrophic plastid.

23. An autoluminescent plant, expressing a functioning luciferase pathway comprising luciferase and one or more luciferin biosynthesis genes integrated in a nuclear genome, wherein said luciferase pathway is obtainable from Collembola, Hemiptera, Diptera (*Arachnocampa luminosa* or *Orfelia fultoni*); Dinoflagellata or Radiolaria (e.g., *Gonyaulax polyedra* or *Thalassicolla* species); Annelids (e.g., *Diplocardia longa, Chaetopterus variopedatus*, or *Odontosyllis* species); Mollusca (e.g., *Pholas dactylus, Watasenia scintillans*, or *Latia* species); Crustacea (e.g., *Vargula hilgendorfii, Cypridina hilgendorfii*, or *Meganyctiphanes norvegica*); Fungi (e.g., *Panellus stipticus* or *Mycena citricolor*); Echinodermata (e.g., *Ophiopsila californica*); or Diplopoda or Chilopoda (e.g., *Luminodesmus sequoiae* or *Orphaneus brevilabatus*).

24. An autoluminescentphytosensor (ALPS) plant monitoring system, comprising:
   (i) an autoluminescent plant of any one of 21-23, wherein activity of said luciferase pathway is induced or complemented by a nucleus-integrated factor;
   (ii) at least one luminescence data detecting sensor positioned on, in proximity to, or remotely from said plant, wherein said sensor detects luminescence emitted from said plant;
   (iii) at least one transmitter that receives said luminescence data from said sensor; and
   (iv) a communication network that receives said luminescence data from said transmitter and conveys it to a receiver.

25. The autoluminescentphytosensor plant monitoring system of any one of 1-4, transgenic plant cell of any one of 5-7, plastids of any one of 8-11, cell of any one of claims 12-15, transgenic or transplastomic plant of 16, plastid of any one of 17-19, or expression cassette of 20, comprising LUX nucleotide sequences shown in SEQ ID NOs:6-10, operably linked for expression, and which are expressed.

26. The autoluminescentphytosensor plant monitoring system of any one of 1-4, transgenic plant cell of any one of 5-7, plastids of any one of 8-11, cell or plastids of any one of 12-15, transgenic or transplastomic plant of 16, plastid of any one of 17-19, or expression cassette of 20, comprising LUX nucleotide sequences shown in SEQ ID NOs:6-11, operably linked for expression, and which are expressed.

27. The autoluminescentphytosensor plant monitoring system, transgenic plant cell, plastids or cell, transgenic or transplastomic plant, or expression cassette of 25 or 26, further comprising, operably linked for expression, the LUX nucleotide sequence shown in SEQ ID NO:12, and which is expressed.

28. The autoluminescentphytosensor plant monitoring system, transgenic plant cell, plastids or cell, transgenic or transplastomic plant, or expression cassette of any one of 25-27, further comprising, operably linked for expression, the LUX nucleotide sequence shown in SEQ ID NO:13, and which is expressed.

29. The plant of any one of 1-4 or 16, further comprising at least one gene or factor that renders said plant incapable of sexual reproduction.

30. The plant of 29, comprising LUX nucleotide sequences selected from the group consisting of:
   i) LUX nucleotide sequences shown in SEQ ID NOs:6-10;
   ii) LUX nucleotide sequences shown in SEQ ID NOs: 6-11;
   iii) LUX nucleotide sequences shown in SEQ ID NOs: 6-10, and LUX nucleotide sequence SEQ ID NO:12;
   iv) LUX nucleotide sequences shown in SEQ ID NOs: 6-11, and LUX nucleotide sequence SEQ ID NO:12;
   v) LUX nucleotide sequences shown in SEQ ID NOs:6-10, and LUX nucleotide sequence SEQ ID NO:13;
   vi) LUX nucleotide sequences shown in SEQ ID NOs: 6-11, and LUX nucleotide sequence SEQ ID NO:13;
   vii) LUX nucleotide sequences shown in SEQ ID NOs: 6-10, and LUX nucleotide sequences SEQ ID NOs:12 and 13; and
   viii) LUX nucleotide sequences shown in SEQ ID NOs: 6-11, and LUX nucleotide sequence SEQ ID NOs:12 and 13.

31. A method of decreasing regulatory requirements necessary for approval of use of a genetically engineered organism, comprising producing said genetically engineered organism employing two or more steps that substitute or eliminate the use of a pathogen, pest, or antibiotic resistance nucleotide sequence in said genetically engineered organism, or that eliminate or reduce the use of a pathogen or a pest in generating said genetically engineered organism.

32. The method of 31, wherein said genetically engineered organism is a transgenic plant, and said steps are selected from the group consisting of:
   i) substituting *Agrobacterium*-mediated transformation with a non-*Agrobacterium* transformation method;
   ii) substituting a pathogenic or pest nucleic acid sequence with a functionally equivalent non-pathogen or non-pest nucleic acid sequence;
   iii) eliminating or removing a selection or antibiotic resistance marker;
   iv) substituting a selection marker with a native allele;
   v) using intragenic or cis-genetic transfer; and vi) using a gene coding for a protein with History of Safe Use (HOSU) or a familiar protein.

33. The method of 32, wherein said non-*Agrobacterium* transformation method is selected from the group consisting of biolistic transformation, whiskers-mediated transformation, microinjection, PEG-mediated transformation, and electroporation.

34. The method of 32 or 33, wherein iv) comprises substituting a mutant allele of rrn16 that confers spectinomycin resistance for a aadA selection marker.

35. A nucleotide sequence encoding a self-enhancing transgene expression loop, comprising:
    a nucleotide sequence of an inducible promoter, operably linked to a transgene of interest, and
    a nucleotide sequence encoding an inducer that induces said inducible promoter, operably linked to, and positioned downstream of, said transgene of interest.

36. Progeny of said plant of any one of 1-4 or 16.

37. The progeny of 36, which are produced sexually or asexually.

38. The progeny of 37, which are produced asexually from cuttings.

39. A part of said plant or progeny of any one of 1-4, 16, or 36-38.

40. The part of said plant or progeny of 39, which is selected from the group consisting of a protoplast, a cell, a tissue, an organ, a cutting, and an explant.

41. The part of said plant or progeny of 39, which is selected from the group consisting of an inflorescence, a flower, a sepal, a petal, a pistil, a stigma, a style, an ovary, an ovule, an embryo, a receptacle, a seed, a fruit, a stamen, a filament, an anther, a male or female gametophyte, a pollen grain, a meristem, a terminal bud, an axillary bud, a leaf, a stem, a root, a tuberous root, a rhizome, a tuber, a stolon, a corm, a bulb, an offset, a cell of said plant in culture, a tissue of said plant in culture, an organ of said plant in culture, and a callus.

42. A method of producing an autoluminescent plant, comprising asexually propagating a cutting of said plant or progeny of any one of 1-4, 16, or 36-38.

Further scope of the applicability of the present invention will become apparent from the detailed description and drawings provided below. However, it should be understood that the detailed description and specific examples, while indicating preferred embodiments of the invention, are given by way of illustration only since various changes and modifications within the spirit and scope of the invention will become apparent to those skilled in the art from this detailed description.

3.0 BRIEF DESCRIPTION OF THE DRAWINGS

The above and other aspects, features, and advantages of the present invention will be better understood from the following detailed descriptions taken in conjunction with the accompanying drawing(s), all of which are given by way of illustration only, and are not limitative of the present invention, in which:

FIG. 1: Shows induction of plant autoluminescence by means of a Genetic Relay Assay, where an activator (e.g., T7 RNA polymerase, T7RNAP) expression is driven by an inducible promoter in the nucleus. When the inducible promoter is stimulated, the T7 RNA polymerase protein will be transcribed and targeted to a plastid (e.g., a chloroplast) using an N-terminally fused plastid transit peptide. The LUX genes in the chloroplast will be driven by the sequence responsive to the activator, e.g., T7 promoter, to which T7 RNA polymerase binds and thus activates LUX transcription.

Figure 2:
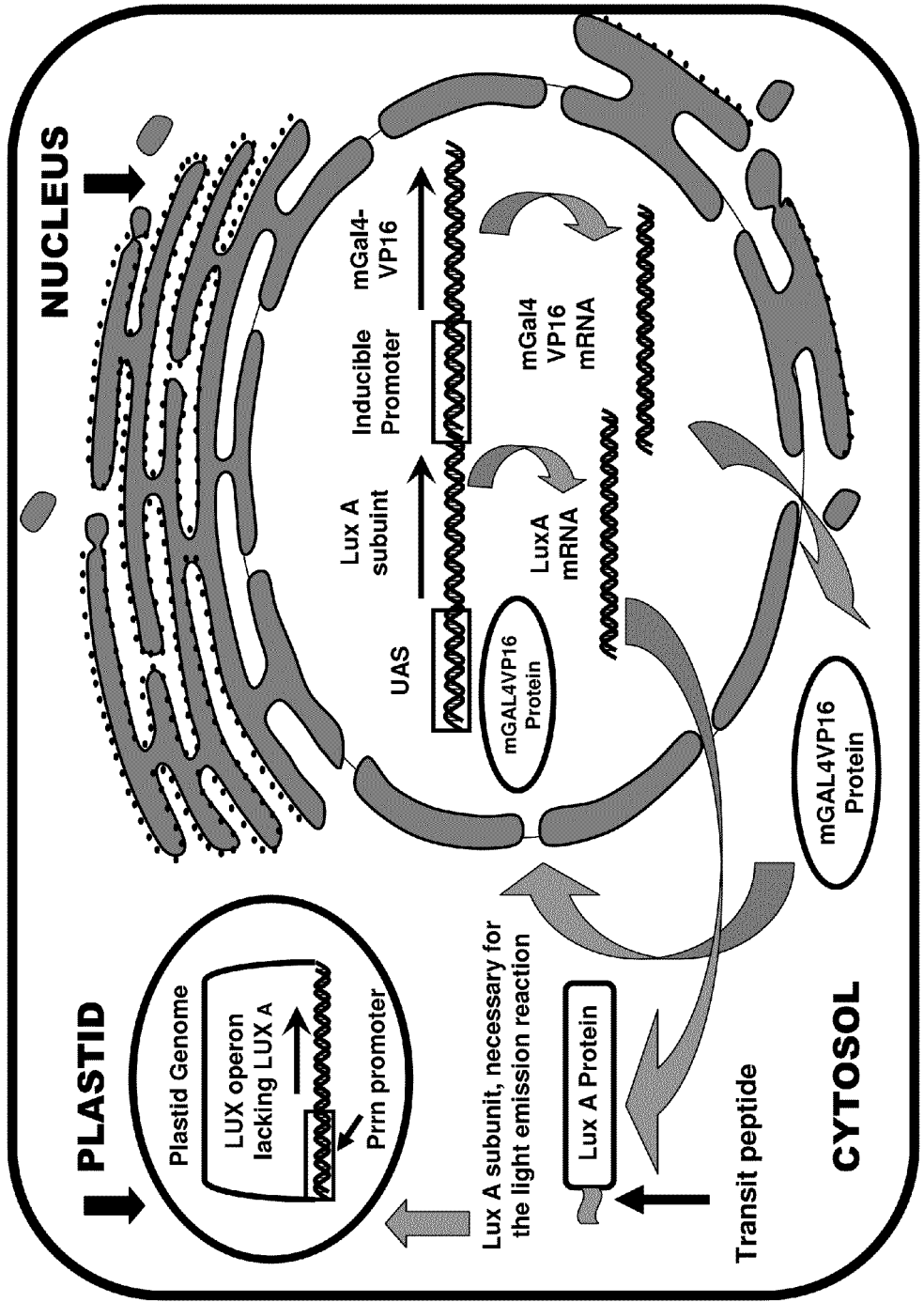

FIG. 2: Shows induction of plant autoluminescence by means of the Genetic Reconstitution Assay. A partial LUX operon, devoid one of the genes required for light emission (e.g., LUX A luciferase subunit), is integrated under a constitutive promoter (e.g., Prrn promoter) into the plastidal genome. The missing LUX A luciferase subunit is introduced under the control of a cis-acting element, e.g., an upstream activating sequence (UAS), into the nucleus. The nucleus also contains an integrated sequence coding for an activator of the cis-acitng element, e.g., mGal4-VP16, driven by an inducible promoter. When the inducible promoter is stimulated, the mGal4-VP16 protein is produced, imported into the nucleus, and activates expression of the LUX A subunit, which in turn is transported into the chloroplast via an N-terminally fused transit peptide. Once LUX A is within the plastid, the fully functional luciferase pathway is reconstituted, and light emission commences.

Figure 3:
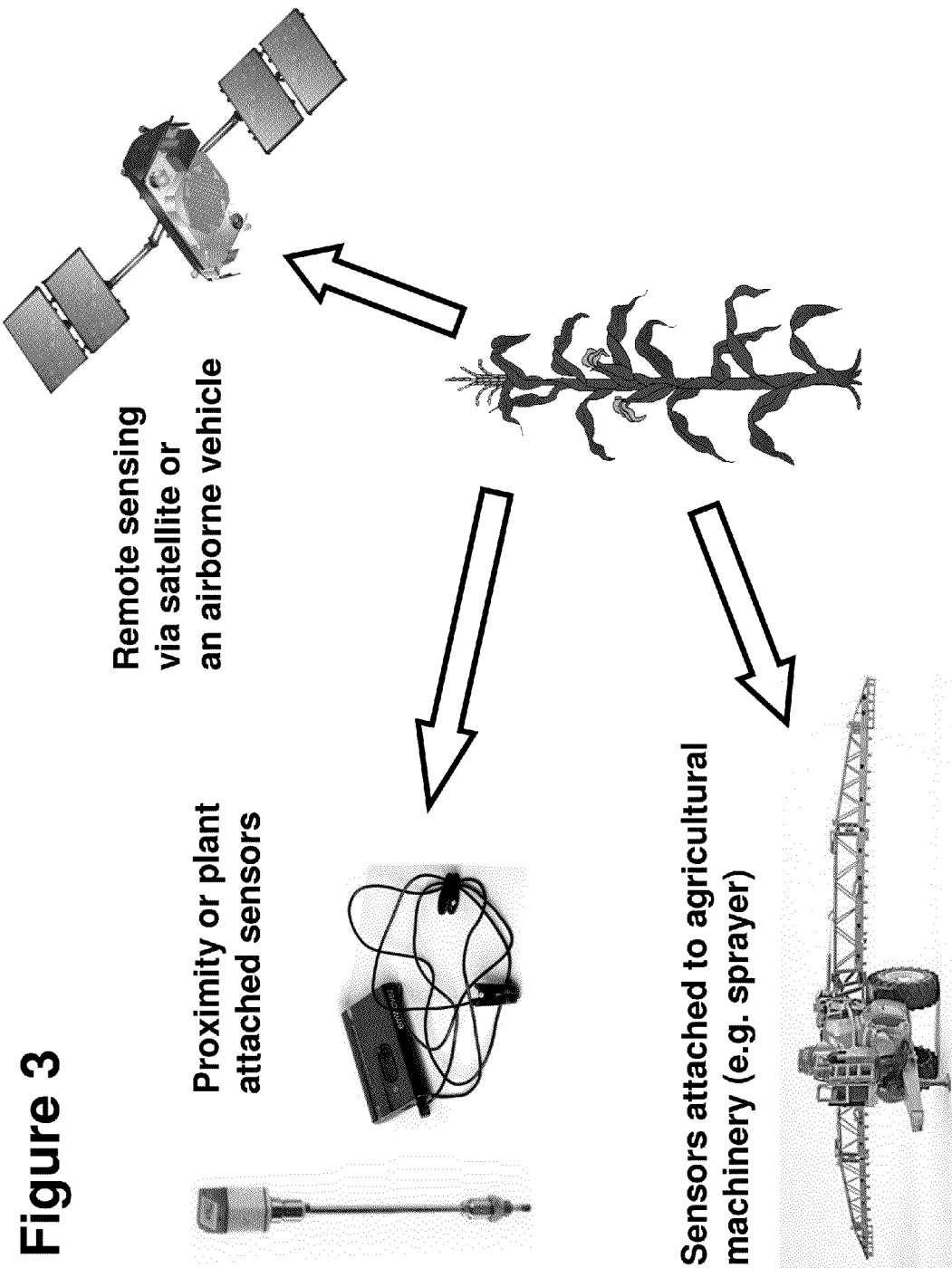

FIG. 3: Shows examples of monitoring of plant light emission.

Figure 4:
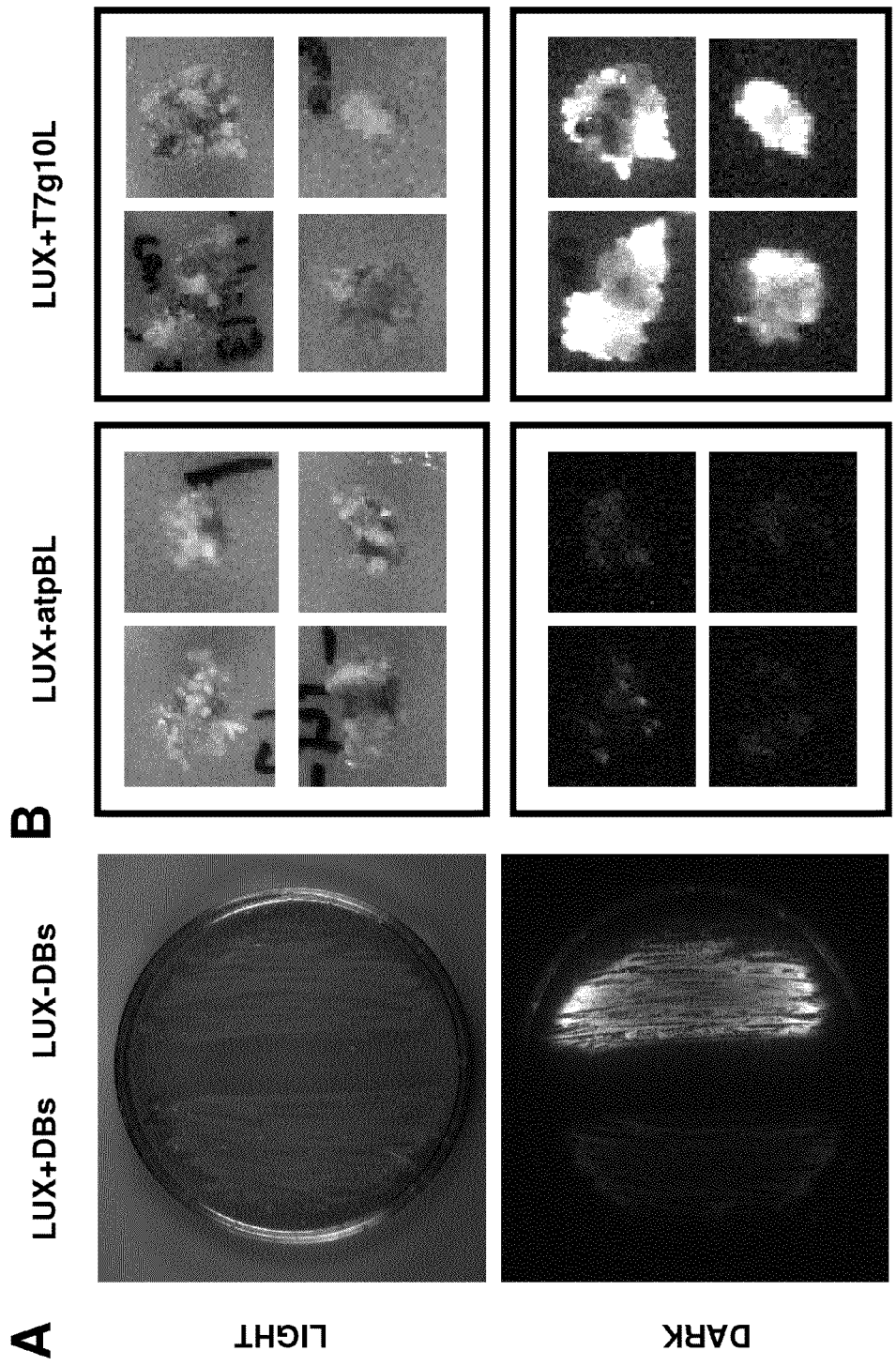

FIG. 4: Shows unexpected and unorthodox effects of various genetic elements on expression of the LUX operon. (A) Addition of 15aa-long TetC DB to LUX A and B subunits essentially abolishes light emission, instead of expected increase. Plated bacterial cultures with and without DBs (LUX+DB and LUX-DB, respectively) are shown. (B) While addition of translational leaders would be expected to enhance light emission in plastids, actual experimental results demonstrate that some leaders (e.g., atbBL) cause a decrease in light emission, while others increase light emission (e.g., T7g10L). Thus, results of modifications of LUX genes with translational leaders cannot be predicted and can only be demonstrated experimentally. Shown are typical transplastomic plants containing LUX genes modified with either atpB or T7g10 leaders (LUX+atpBL and LUX+T7g10L, respectively) regenerating from callus in tissue culture. Light emission detected using ChemiDoc XRS Molecular Imager, inverse images shown.

Figure 5:
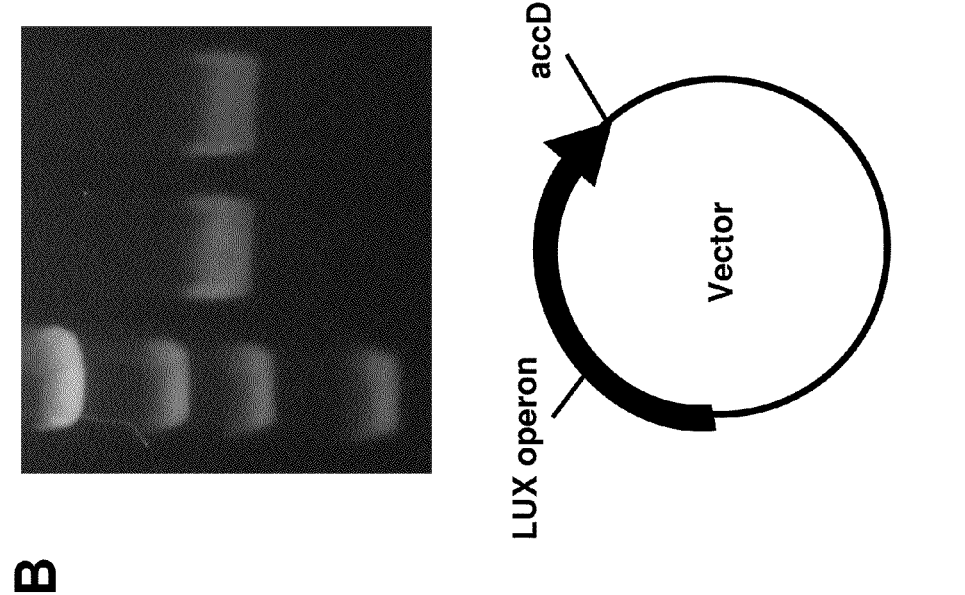
Figure 5:
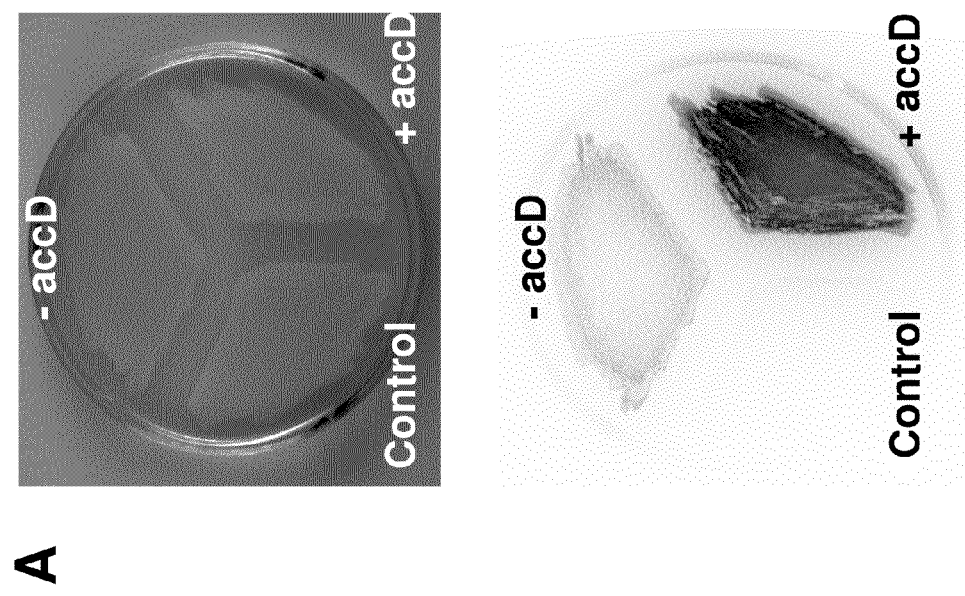

FIG. 5: Shows enhancement of light emission of the LUX operon by co-expression with plastidal accD. (A) Bacterial cultures of *E. coli* expressing LUX operon with ("+accD") or without ("–accD") accD, or control cultures not containing LUX operon or accD ("Control"), were imaged using Chemi-Doc XRS Molecular Imager. Upper panel: culture plates in light; Lower panel: photographic exposure of the plates. (B) accD DNA fragment cloned and co-expressed with the LUX operon; marker 1kb NEB (upper panel); schematic representation of the expression vector containing the LUX operon and the plastidal accD (lower panel).

Figure 6:
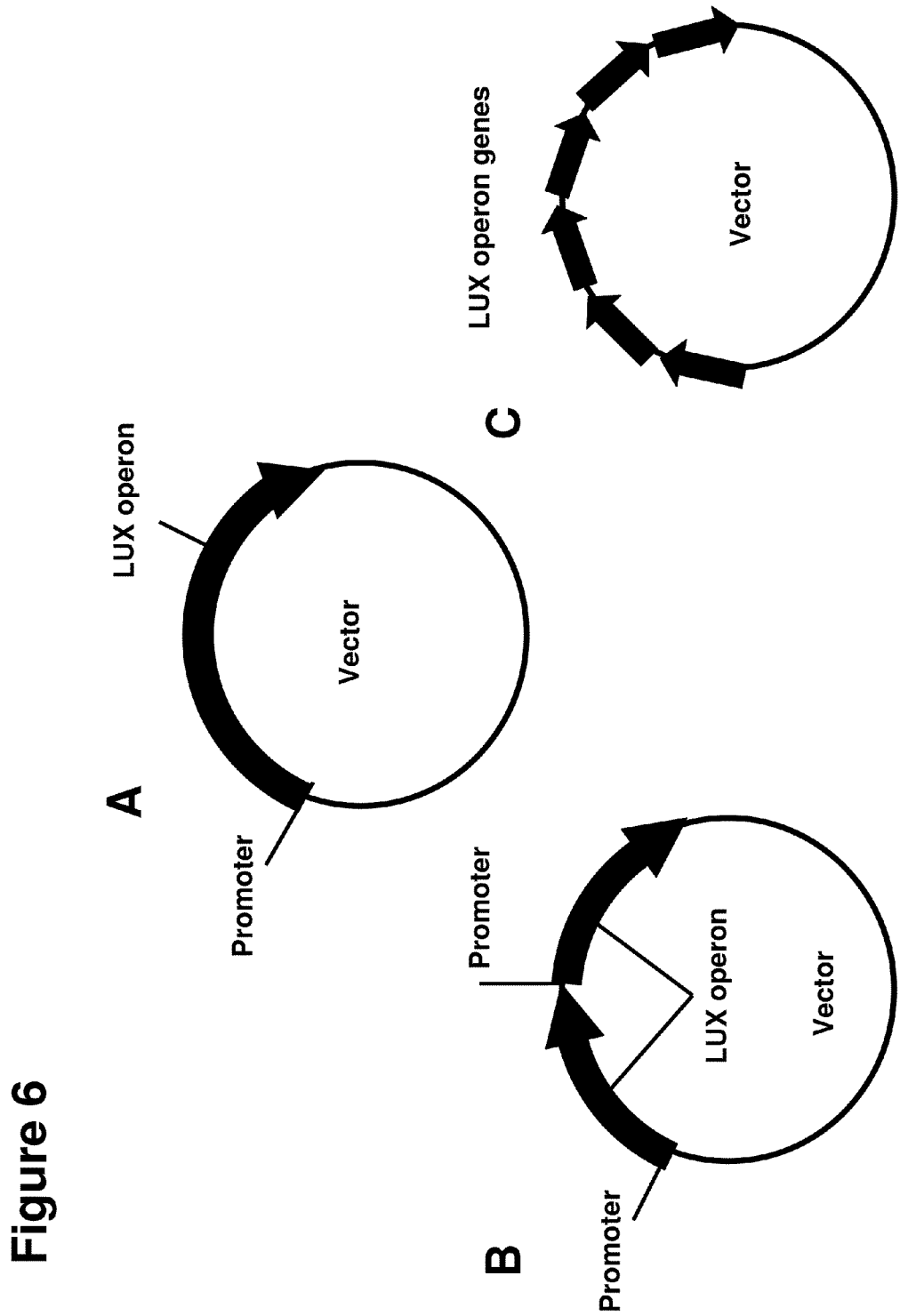

FIG. 6: Shows options for expressing LUX operon on a single vector in a plastid of a plant cell. (A) LUX genes expressed in the form of an operon; (B) an additional promoter introduced between the LUX genes to enhance transcription of the LUX genes. While one additional promoter is shown, multiple promoters can be used; (C) Genes of the LUX operon, together constituting a complete and fully functional luciferase pathway, expressed from separate promoters on a single vector.

Figure 7:
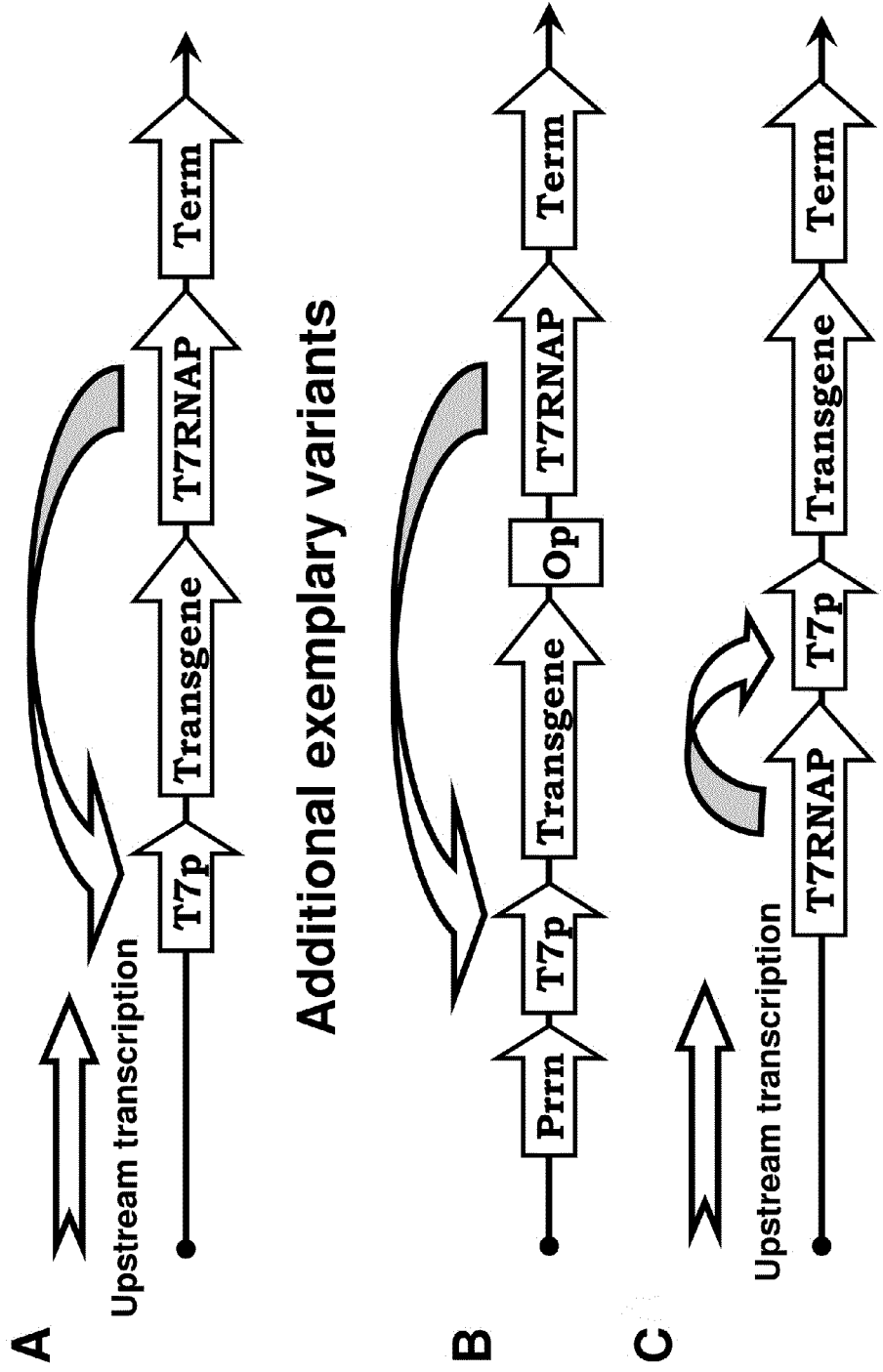

FIG. 7: Shows increasing transgene expression via a self-enhancing transgene expression loop. An activator-inducible promoter (e.g., T7 promoter) is placed upstream of a transgene that requires enhanced expression, followed by an activator (e.g., T7 RNA polymerase) that activates the inducible promoter. The initial levels of T7RNA polymerase are produced by transcription upstream of the expression cassette. For example, (A) transcription of the expression cassette integrated into the TrnI/TrnA region of the chloroplast genome can be induced by the read-through transcription from the upstream native Prrn promoter. Once initial copies of the T7RNAP polypeptide are produced, they bind to the T7 promoter and continue transcribing the expression cassette. Additional T7RNAP copies produced enhance the transcription of the expression cassette even further, and so on and so forth, thus causing a self-enhancing positive feedback loop. Many variants of the self-enhancing transgene expression loop can be envisioned. In certain embodiments (B,C), preferred combinations contemplate the use of operator sequences, promoters directly upstream to inducible promoter to produce initial T7RNAP transcripts, and placing T7RNAP upstream to T7 promoters. Abbreviations: T7p—T7 promoter; Term—a terminator; T7RNAP—T7 RNA polymerase; Op—an operator, e.g. LacO; Prrn—Prrn promoter.

Figure 8:
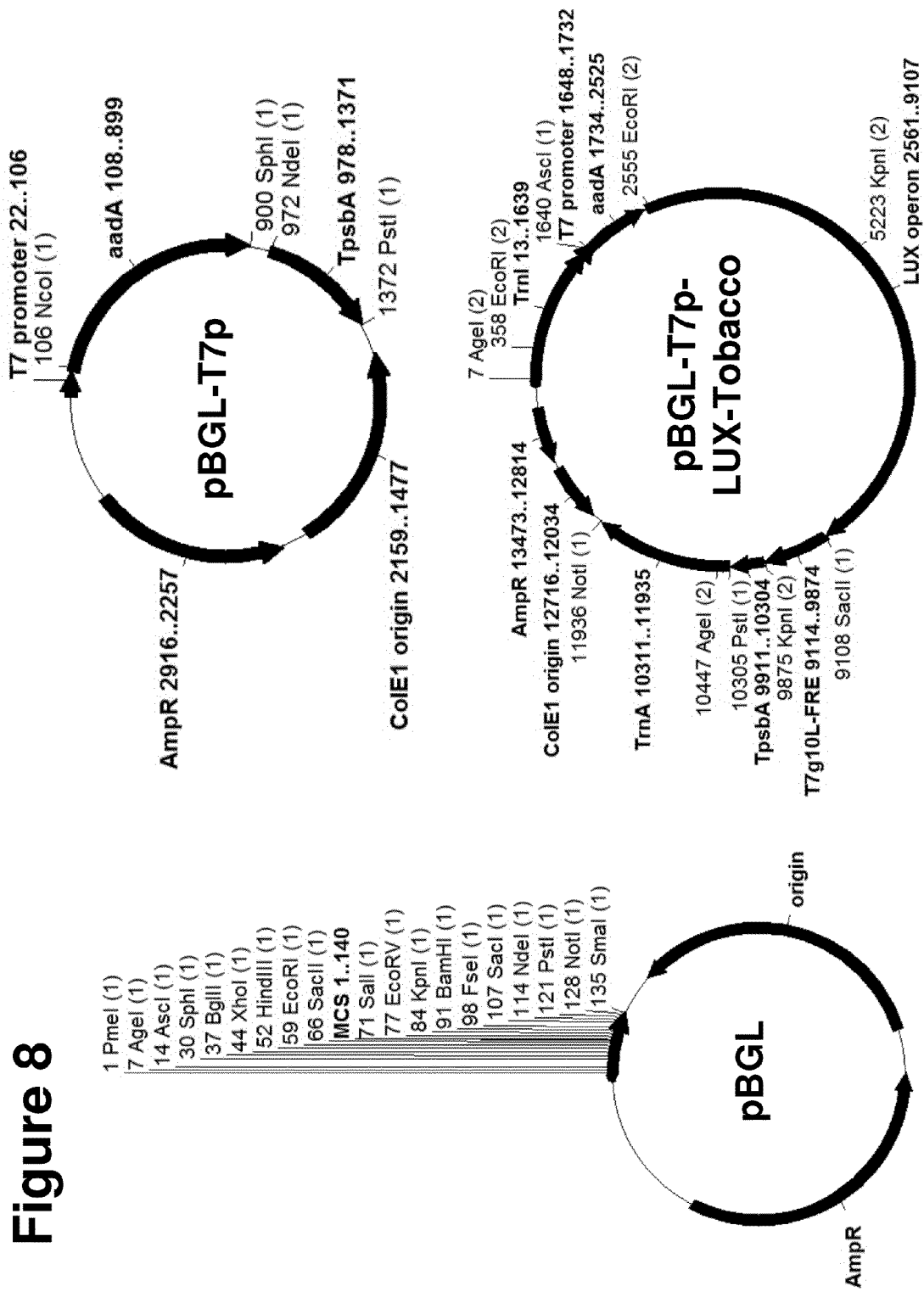

FIG. 8: Shows maps of vectors pBGL, pBGL-T7p, and pBGL-T7p-LUX-Tobacco. Abbreviations: T7g10—T7 promoter; aadA—spectinomycin resistance gene; TpsbA—psbA terminator; Fre—E. coli Fre gene; TrnI and TrnA—tobacco homologues recombination sequences.

Figure 9:
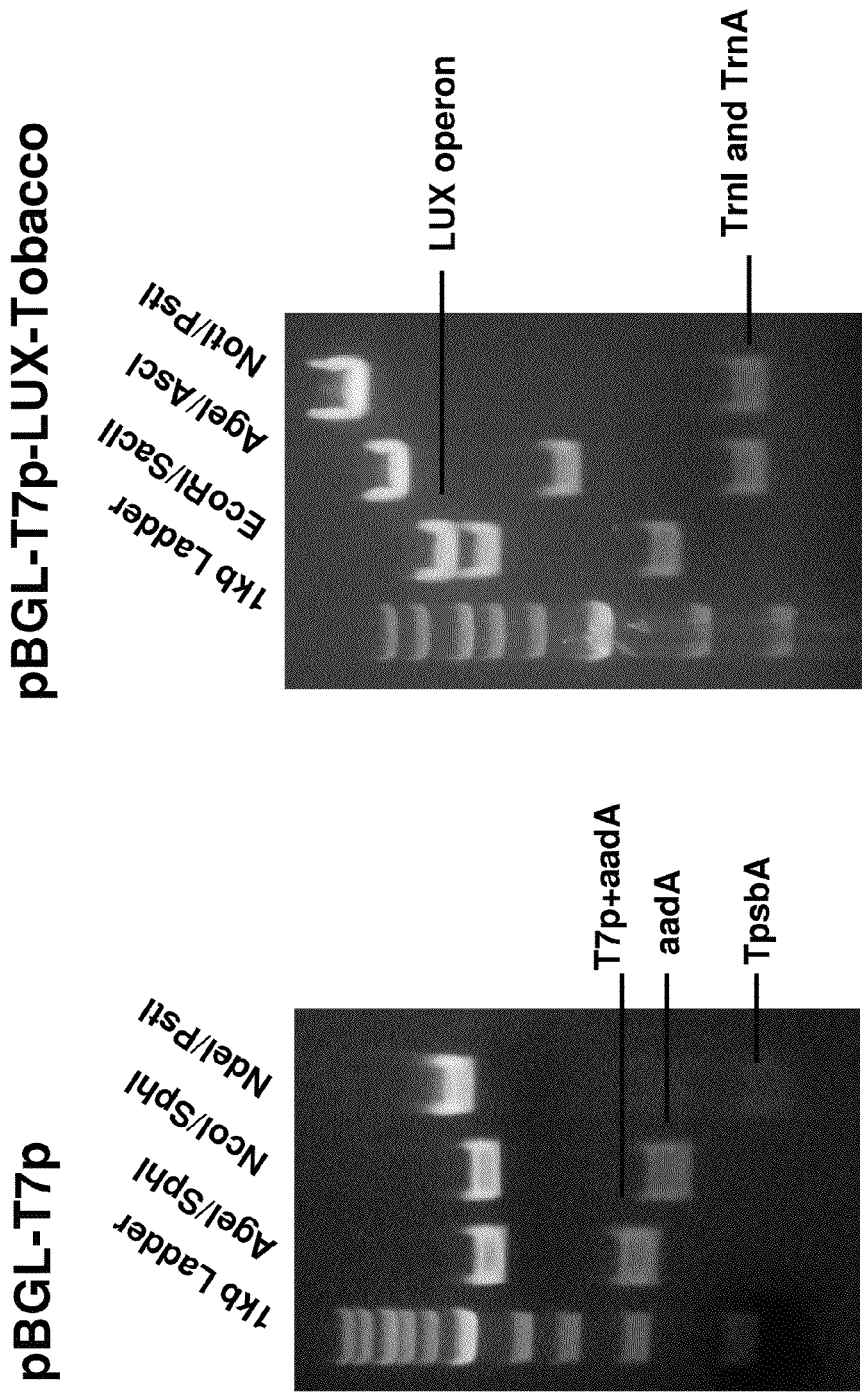

FIG. 9: Shows exemplary restriction digest of vectors pBGL-T7p and pBGL-T7p-LUX-Tobacco. Bands corresponding to the promoter, aadA gene, and the terminator are shown for pBGL-T7p; bands corresponding to the LUX operon, TrnI, and TrnA sequences are shown for pBLG-T7p-LUX-Tobacco; 1 kb Ladder (NEB) used for standard.

Figure 10:
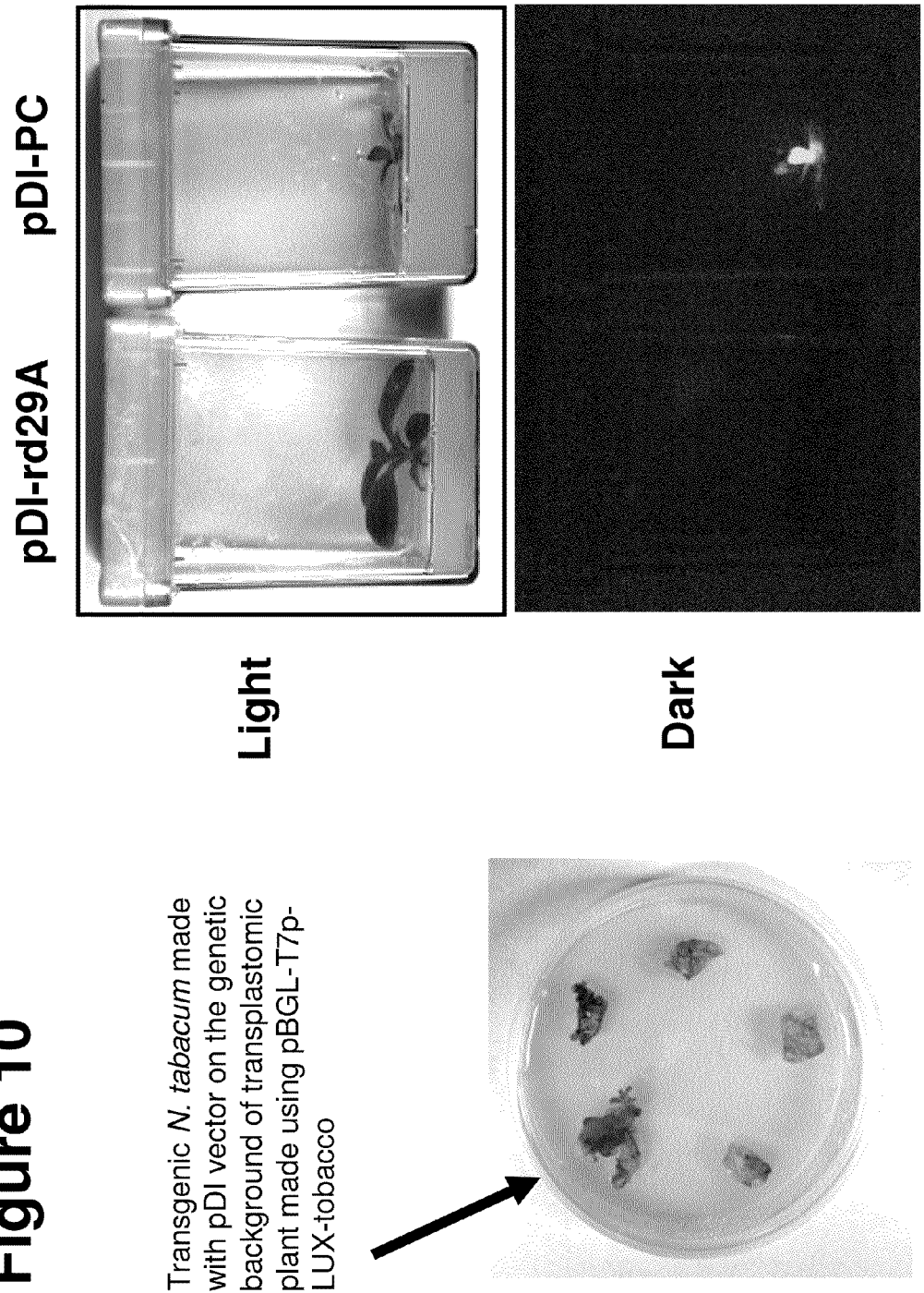

FIG. 10: Shows ALPS plants. (A) Transgenic N. tabacum plant produced using one of the pDI vectors on genetic background of a transplastomic tobacco plant made using pBGL-T7p-LUX-Tobacco vector; (B) Transgenic plants in high humidity conditions (magenta box) containing LUX operon driven by T7 promoter integrated into plastidal genome and expressing T7RNAP under drought-inducible rd29A promoter (left-hand plant, pDI-rd29A), silent under high humidity conditions, as compared to T7RNAP driven by constitutive NOS promoter (right-hand plant, pDI-PC) under the same conditions. Images taken using BioRad ChemiDoc XRS Molecular Imager, inverse image shown.

4.0 DETAILED DESCRIPTION OF THE INVENTION

The following detailed description of the invention is provided to aid those skilled in the art in practicing the present invention. Even so, the following detailed description should not be construed to unduly limit the present invention, as modifications and variations in the embodiments herein discussed may be made by those of ordinary skill in the art without departing from the spirit or scope of the present inventive discovery.

The contents of each of the references discussed in this specification, including the references cited therein, are herein incorporated by reference in their entirety.

4.1 Autoluminescnet Phytosensor Plants (ALPS) and Related Methods 4.1.1 Autoluminescent Plants The term "autonomously luminescent" or "autoluminescent" as used herein refers to a plant or plant cell genetically engineered to comprise a fully functional luciferase pathway, rendering the plant or cell capable of emitting light. The transgenic autoluminescent plant, as used herein, includes at least one plant cell. A "plant cell" refers to any cell of a plant, either taken directly from a seed or plant, or derived through culture from a cell taken from a plant. A plant cell includes, for example, cells from undifferentiated tissue (e.g., callus), plant seeds, propagules, gametophytes, sporophytes, pollen, microspores, and embryos.

In one aspect, the present invention relates to a transgenic autoluminescent plant based on a bacterial LUX operon expressed from a plant plastidal genome. The plant includes a heterologous nucleotide sequence, which includes a bacterial LUX operon, including LUX A, LUX B, LUX C, LUX D, LUX E, and LUX G genes, which may or may not contain additional transgenes. The LUX operon is integrated within a plastid (e.g., a chloroplast) genome. The LUX operon can be derived from any luminescent bacterium. Examples of a nucleotide sequence encoding the full LUX operon is presented in GenBank under accession numbers AY341062 (*Vibrio fischeri* [*Vibrio fischeri* strain ATCC 7744 lux operon, complete sequence]; EU192082 (*Vibrio harveyi* [*Vibrio harveyi*iBCB440 lux operon, complete sequence]); AF403784 (*Photorhabdus luminescens*, (formally referred as *Xenorhabdus luminescens* [*Photorhabdus luminescens* lux operon, complete sequence]); and AB261992 (*Shewanellahanedai* [*Shewanellahanedai* lux operon (luxC, luxD, luxA, luxB, luxE, luxG) genes and flanking regions, strain: NCIMB 2157]); and M63594 (*Photobacterium leiognathi*, strain ATCC 25521); and DQ988873 (*Photobacterium phosphoreum* [*Photobacterium phosphoreum* strain ATCC 11040, complete LUX and RIB operons]).

Other combinations of luciferin/luciferase can potentially be employed to generate autoluminescent plants. Genes encoding for luciferase and biosynthesis of corresponding luciferin can be expressed in the form of synthetic operons in plant plastids. The term "operon" refers to a nucleotide sequence which codes for a group of genes transcribed together. The term "gene" refers to chromosomal DNA, plasmid DNA, cDNA, synthetic DNA, or other DNA that encodes a peptide, polypeptide, protein, or RNA molecule, and regions flanking the coding sequence involved in the regulation of expression. Some genes can be transcribed into mRNA and translated into polypeptides (structural genes); other genes can be transcribed into RNA (e.g., rRNA, tRNA); and other types of genes function as regulators of expression (regulator genes). Alternatively, luciferase and luciferin biosynthesis genes can be expressed as monocistronic units in a plant's nucleus. Examples of expressed luciferase/luciferin biosynthesis genes include, but are not limited to, luciferase pathways from Cnidaria (Coelenterates); or Ctenophores (e.g. *Aequorea Victoria, Periphylla periphylla,* or *Renilla reniformis,* or *Obelia* or *Mnemiopsis* species); or orders of Coleoptera, Collembola, Hemiptera, Diptera (e.g. *Photinus pyralis,* or *Arachnocampa luminosa* or *Orfelia fultoni*); or Dinoflagellata or Radiolaria (e.g., *Gonyaulax polyedra* or *Thalassicolla species*); or Annelids (e.g., *Diplocardia longa,* or *Chaetopterus variopedatus* or *Odontosyllis* species); or Mollusca (e.g. *Pholas dactylus,* or *Watasenia scintillans* or *Latia* species); or Crustacea (e.g. *Vargula hilgendorfii,* or *Cypridina hilgendorfii,* or *Meganyctiphanes norvegica*); or Fungi (e.g. *Panellus stipticus* or *Mycena citricolor*); or Echinodermata (e.g. *Ophiopsila californica*); or Diplopoda or Chilopoda (e.g. *Luminodesmus sequoiae* or *Orphaneus brevilabatus*). One skilled in the art can further appreciate that genes encoding for the luciferase or luciferin biosynthesis genes can be further optimized for expression in a given cellular compartment or environment, and be integrated in nuclear, plastidal, or mitochondrial genomes, or otherwise stably expressed in a plant cell. Methods of cloning of corresponding genes and producing transgenic or transplastomic plants are known in the art.

4.1.2. Autoluminescet Phytosensor Plants (ALPS)

Autoluminescent phytosensor plants described herein are based on activation of a functional luciferase pathway integrated into a plastidal genome as a result of a certain stimulus or condition, using inducible sequences described herein and in the section "Inducible Promoters" below.

In one aspect, the invention relates to direct activation of a plastid-integrated luciferase pathway by a stimulus. For example, certain plastidal promoters are known to be activated by a stimulus, e.g., the light-activated PpsbA promoter can drive direct expression of the LUX operon in the plastid. Thus, plastid genome-integrated luciferase pathway expression can be activated directly by a stimulus.

In another aspect, the invention relates to indirect activation of the luciferase pathway in response to a stimulus. Examples of indirect activation include genetic relay and genetic reconstitution assays (FIGS. 1 and 2).

In one embodiment, the genetic relay assay (FIG. 1) contemplates integration of LUX operon, or any other luciferase pathway, into plastidal genome. Expression of the LUX operon is driven by an inducible element, e.g., a T7 promoter. Then, a sensory element, such as an inducible promoter, driving an activator of the plastid-integrated luciferase pathway, e.g., T7 RNA polymerase (T7RNAP) is integrated into the nuclear genome. When the nucleus integrated inducible promoter is activated by a certain stimulus (e.g., drought, nutrient deficiency, pests, etc.) it commences the expression of the T7 RNA polymerase expression which, in turn, is localized to the plastid via an N-terminal targeting transit peptide. Once T7RNAP is within the plastid, it binds to the T7 promoter and activates expression of the LUX operon, and the ALPS commence to glow in response to the stimulus.

In yet another embodiment, the luciferase pathway can be activated in response to a stimulus via a genetic reconstitution assay (FIG. 2). Here, partial LUX operon lacking one of the genes required for light emission, for example LUX A subunit, is integrated under a constitutive promoter into the plastidal genome. While the partial LUX operon is expressed in the plastid, light emission does not occur since the luciferase lacks one of its subunits for functionality. The missing LUX A luciferase subunit is introduced under the control of a cis-acting element, such as an upstream activating sequence (UAS), into the nucleus. The nucleus also contains an integrated gene coding for an activator of the cis-acitng element, e.g., mGal4-VP16, driven by an inducible promoter. When the inducible promoter is activated by a stimulus (e.g., drought, nutrient deficiency, pests, etc.), the mGal4-VP16 protein is produced, imported into the nucleus, and activates expression of LUX A subunit, which in turn is transported into the chloroplast via an N-terminally fused transit peptide sequence. Once within the chloroplast, the fully functional luciferase pathway is reconstituted and light emission commences.

ALPS plants can be based on luminescence systems other than the LUX operon, such as those derived from bioluminescent pathways of Cnidaria (Coelenterates); or Ctenophores (e.g. *Aequorea Victoria, Periphylla periphylla*, or *Renilla reniformis*, or *Obelia* or *Mnemiopsis* species); or orders of Coleoptera, Collembola, Hemiptera, Diptera (e.g. *Photinus pyralis*, or *Arachnocampa luminosa* or *Orfelia fultoni*); or Dinoflagellata or Radiolaria (e.g., *Gonyaulax polyedra* or *Thalassicolla* species); or Annelids (e.g., *Diplocardia longa*, or *Chaetopterus variopedatus* or *Odontosyllis* species); or Mollusca (e.g. *Pholas dactylus*, or *Watasenia scintillans* or *Latia* species); or Crustacea (e.g. *Vargula hilgendorfii*, or *Cypridina hilgendorfii*, or *Meganyctiphanes norvegica*); or Fungi (e.g. *Panellus stipticus* or *Mycena citricolor*); or Echinodermata (e.g. *Ophiopsila californica*); or Diplopoda or Chilopoda (e.g. *Luminodesmus sequoiae* or *Orphaneus brevilabatus*). If genes of the bioluminescent systems are expressed in the form of a synthetic operon in plant plastids, they can be activated indirectly similarly to LUX-operon based ALPS. If those bioluminescent systems are expressed from the nuclear DNA, they can be activated by being directly driven by an inducible promoter.

4.1.3 Transgenic Organisms and Plants Designed, Engineered, or Contemplated for Decreased Regulatory Requirements Deregulation of transgenic plants and other organisms for commercialization is an expensive and time-consuming matter. Deregulation of a transgenic plant may cost tens of millions of dollars and take several years to achieve. Reducing deregulation costs of any transgenic organism is highly commercially attractive.

A phenotypically/genetically equivalent transgenic plant can be engineered in many ways. Here we claim a method comprised of steps intended for engineering of transgenic crops, or other organisms, with decreased regulatory requirements. For example, to overexpress gene A in plant X in a plant, one may use the strong viral CaMV35S promoter and introduction of the expression cassette into the plant's nuclear genome using *Agrobacterium*-mediated transformation. However, overexpression of gene A in plant X can also be achieved by using strong plant promoter, such as the Ubiquitin promoter, and the expression cassette can be introduced using biolistic bombardment. The first method uses plant pest sequences, while the second method does not, which subjects plants made by the first method to much higher regulatory requirements than a plant made by the second method. While both methods result in a similar plant X overexpressing transgene A, deregulation of a plant made by the first method will be significantly more costly and time consuming as compared to the plant made by the second method.

In the above example, the bombardment method is typically less effective in generating transgenic plants than using *Agrobacterium*-mediated transformation. Thus, use of a technically less effective method may demonstrate intent to do so in order to ease deregulation. While solitary steps (e.g., use of plant promoters instead of CaMV35S) might be customary in certain routine research projects, the claimed method constitutes two or more steps directed towards reducing deregulation of the same transgenic plant.

Although this aspect of the invention is illustrated in conjunction with an example, it is evident that many alternatives, modifications, and variations of the method will be apparent to those skilled in the art. Accordingly, any combination of, or use of, approaches aimed at easing the deregulation burden are deemed to be encompassed by the method. Some examples of approaches that can constitute steps of the method are demonstrated below.

One such example can include the use of natural plant alleles instead of selection markers. For example, a natural plant allele comprising a mutation in the small ribosomal RNA (rrn16) gene confers resistance to spectynomicin and can be used instead of the known selection marker aadA, thus potentially eliminating the need for marker excision for successful deregulation of a transgenic crop. Using the native allele instead of a selection marker can be construed as designing a crop for easing deregulation. Another technique that may constitute an indication of the method is selection marker removal as known in the art.

In another example, use of genes encoding for "familiar proteins" can be indicative of the use of the method. "Familiar proteins" are proteins known to have been previously consumed as food or feed, or have track record of safe exposure to human or animals, or otherwise have a History of Safe Use (HOSU). It is also beneficial to move away from use of potential pest and microbial genes, and use plant genes to achieve the same phenotypical result. Especially undesirable are DNA sequences designated under 7 CFR 340, or organisms classified as pathogens (for example, *Agrobacterium*), pests (for example, pest plants or other pests) or unknown organisms. Preferred DNA sequences are from organisms that are not pests, from plants, from well characterized material, and non-coding regulatory regions. The method encompasses engineering or substitution of undesired sequences with the preferred sequences.

In yet another example of the invention, intragenic and cis-genetic transfer of genes from one plant to another as a safe alternative is contemplated. This includes, for example, the transfer of beneficial genes lost during domestication from a wild plant into a domesticated variety. These types of transfers are especially beneficial since they might not require deregulation at all.

The method of present invention is applicable to plants, or to other transgenic organisms such as genetically modified farm animals or commercial varieties of fish.

4.1.4 Monitoring and Survey

According to one aspect of the present invention, there is provided a system for monitoring of ALPS comprising at least one sensor positioned on a plant, in proximity to a plant (e.g., pivot sprinkler irrigation system), or remotely to a plant (e.g., satellite, drone, or UAV or any other type of aircraft) (FIG. 3), a transmitter, and a communication network conveying the sensor-collected data. Examples of communication networks can include a telephone network, a cellular telephone network, a computer network, a satellite network, or a combination of any two or more of these. Computerized networks are highly preferable.

One preferred embodiment of the invention includes at least one sensor and at least one transmitter for transmitting a signal including the data. The invention can also include at least one receiver receiving a command signal, as well as at least one storage device for storing the collected data. Yet another embodiment includes a network selected from the group consisting of a telephone network, a cellular telephone network, a computer network, a satellite network, and a combination of any of these, and the network may integrate wire and/or wireless communication, and may include at least one user client.

In another aspect of the invention, the spectrum of light emission of the luciferase can be modified by methods known in the art, e.g., mutagenesis or co-expression of fluorescent proteins. Thus different stimuli can initiate light emission of different wavelengths from the same plant, or from different plants, which might be advantageous under different conditions or for different purposes.

4.2. Improvements of Autoluminescent Plants Comprising LUX Operon Genes 4.2.1 Unexpected Characteristics of Functional Genetic Elements in Enhancement of LUX Operon Light Emission in Transplastomic Plants Various genetic elements, e.g., prokaryotic, eukaryotic, organellar, viral, and others, are known in the art to enhance expression of transgenes. In the case of plastids, the art describes certain elements that can improve transgene expression, for example downstream boxes (DBs) and translational leaders. Unexpectedly, the effects of these and other genetic elements on LUX operon expression in plastids was found to be completely unpredictable. For example, downstream boxes (e.g., 15α-long TetC DB (FIG. 4A) or 5α-long Ec/DB), known in the art to enhance and improve transgene expression and thus expected to augment light emission of plastid-expressed LUX operon, when fused to LUX A and B subunits, have caused a dramatic decrease in light emission. Essential abolishment of light emission of the LUX operon containing DB sequences fused to luciferase subunits A and B, as compared to constructs without DBs, is contradictory to the expected enhancement of light emission. This effect has been observed in both bacteria and transplastomic plants carrying DB-containing LUX transgenes as compared to control constructs without DB boxes. Thus, unexpectedly, the LUX operon has behaved in an unpredictable and opposing manner when use of elements known in the art has been attempted.

In another example, the art teaches that addition of transcriptional leaders is expected to enhance expression and activity of transgenes in plant plastids. Several translational leaders have been experimentally tested for their ability to increase activity of the LUX genes and the results, again, were unexpected and diverse. For example, addition of atpB leaders to LUX genes expressed in plastids has caused reduced light emission, while addition of T7g10 leaders caused increased light emission (FIG. 4B). Thus, while contemporary art suggests that translational leaders should lead to enhanced transgene expression, in the case of the LUX operon, the effect can only be established empirically since different types of translational leaders produced different, and opposing, unpredictable effects.

In yet another example, the effect of the use of intercistronic expression elements (IEE) (e.g., Zhou et al, (2007) "Identification of a plastid intercistronic expression element (IEE) facilitating the expression of stable translatable monocistronic mRNAs from operons." Plant J.; 52(5): 961-72; 5'-TAGGATCGTTTATTTACAACGGAATGG-TATACAAAGTCAACAGATCTCAA-3' (SEQ ID NO 1) on expression of LUX genes was not known. In contemporary art, IEE elements are thought to function by directing RNA cleavage and evidently serving as binding site for pentatricopeptide repeat (PPR) proteins. While here we provide, by way of example only, the use of SEQ ID NO:1, other PPR binding sites known in the art can be used in the present invention. Extensive experimentation with SEQ ID NO:1 has demonstrated that plastid transformation vectors containing IEE sites introduced between LUX genes, and particularly in instances where LUX genes of the vectors have been driven by the classical bacterial Shine-Dalgarno (SD) sequence AGGAGG ribosome binding site, or T7g10, or the rbcL leader sequences, produced transplastomic autoluminescent plants with superior light emission properties, multiple fold brighter than the control plants. Particularly preferable combinations of IEE/leader sequences were those where all of the LUX operon genes have been separated by the IEE sites, and further, the luciferase subunits LUX A and B have been driven by the T7gL leader and the rest of the LUX genes (C-D-E or C-D-E-G) driven by either rbcL or the bacterial SD sequence. Transformation vectors in which all of the LUX subunit have been separated by IEE sites and driven by either rbcL or classical SD sequence have also produced enhanced light output as compared to the control plants. However, when the GFP gene was preceded by an IEE site at its 5' terminus, positioned similarly to the IEE preceding the LUX genes, has been placed in a vector downstream of IEE-containing LUX operon, no GFP expression could be detected in transplatomic plants made with the vector.

This negative result demonstrates that the effect of IEE on a specific luminescent or fluorescent gene cannot be predicted, being dependent on the specific ORF expressed, position within the operon, and other factors. Thus, the effects of IEE on expression in cases of luminescent or fluorescent proteins, such as LUX proteins or GFP, can only be determined experimentally, and cannot be anticipated. In yet another instance, in transformation vectors where all of the LUX subunits have been separated by IEE sites and driven by the T7g10 leaders, the expression cassette became genetically unstable, spontaneously losing large pieces of DNA, preventing generation of autolumniescent plants.

4.2.2 Autoluminescent Plants with Altered Size, Shape, and/or Number of Plastids Modifications in the expression of chloroplast division genes have been known to produce altered forms of chloroplasts. Particularly, modifications in expression of plant Min and other chloroplast division-related genes have been known to generate macrochloroplasts, where a plant cell contains a reduced number of abnormally large chloroplasts, or minichloroplasts, where a plant cell contains a large number of smaller chloroplasts (e.g. Colletti et al, Current Biogloy (2000), 10:507-16; Reddy et al, Planta (2002), 215:167-76). Note also U.S. Pat. No. 6,982,364.

Enlarged chloroplasts (e.g., macrochloroplasts) can be instrumental for improvement of chloroplast genetic modification methods, particularly by bombardment, since they present larger targets for particle penetration. To generate plants with macrochloroplasts and thus improved transformation capacity, we have overexpressed the tobacco MinD gene (NtMinD, GeneBank EF606850) in transplastomic autoluminescent plants containing plastid-expressed LUX operon. NtMinD, driven by the NOS promoter and terminator, have been cloned into pCAMBIA1300 vector and used to produce NtMinD-overexpressing transgenic plants on the background of transplastomic autoluminescent plants using *Agrobacterium*-mediated transformation.

The art teaches that in instances of alteration of chloroplast shape or size, for example using overexpression of Min genes, there is a compensation in chloroplast number, and overall cellular plastidal volume remains constant (Reddy et al, Planta (2002), 215:167-76). Therefore, light output of the NtMinD overexpressing autoluminescent plants was not expected to change. However, unexpectedly, autoluminescent plants with altered chloroplast size have exhibited a notable increase in light emission in tissue-culture regenerating plants as compared to control plants. Similar results of enhanced light emission have been noticed when other genes regulating chloroplast shape and size, including *Arabidopsis* (AtMinD1 [At5g24020] and AtMinE1 [At1g69390]) and bacterial genes (e.g., *E. coli* EcMinD or EcMinC [GeneBank J03153], translationally fused to rubisco plastid targeting peptide), have been overexpressed in transplastomic autoluminescent plants. One skilled in the art can appreciate that a variety of genes involved in plastidal division processes (e.g., FtsZ, ARC, etc.) can be used to generate transgenic plants with altered chloroplast shape, size, and/or number on the background of transplastomic autoluminescent plants, thus modifying light emission, and the present invention encompasses all such possibilities.

4.2.3 Enhancement of LUX Operon Light Output by accD, a Subunit of Plant Acetyl-CoA Carboxylase, and by Multiple Promoters In plants, overexpression of acetyl-CoA carboxylase (ACCase) subunit accD (SEQ ID NO:2) has been known to influence fatty acid content in certain plant tissues (Madoka et al, Plant Cell Physiol. 43(12): 1518-1525 (2002) and JP2001000300038). However, it was not known if accD would have any effect on substrates of the bacterial luciferase, nor if overexpression accD or its co-expression with the LUX operon would have any effect on light emission.

Experimentally, we have discovered that overexpression of the plant accD enhances light output of the LUX operon. For example, accD co-expressed with the LUX operon in bacteria has resulted in cultures several fold brighter than those lacking accD (FIG. 5A). These results demonstrate that accD can be potent enhancer of LUX operon mediated light emission.

In yet another aspect of the present invention, while in the described LUX-operon based autoluminescent plants LUX genes are introduced into a chloroplast genome in the form of a single operon driven by a single promoter (FIG. 6A), the operon can be further split by an additional promoter sequence to enhance transcription of the downstream genes (FIG. 6B), or each gene of the operon can be driven by a separate promoter (FIG. 6C), which may further enhance transcription of the individual LUX genes and thus generate brighter autoluminescent plants.

4.2.4 Transformation of Ornamental Species

Transformation of plastids of ornamental plant species can be useful for generation of ornamental phytosensors, as well as for new varieties of constitutively glowing ornamental plants. Plastid transformation of certain varieties of Solanaceae species (e.g., tobacco or *petunia*) have been known in the art. However, it is also known that a great variability in regeneration and transformation capacity exists between different, frequently very close, cultivars of the same species. For example, protocols for regeneration and transformation of *N. tabacum* cv. Samsun and Xanthi are known; however, these methodologies are ineffective on *N. tabacum* cv. Wisconsin 38. Similarly, while regeneration and transformation protocols for certain *petunia* cultivars (e.g., Pink Wave) are known, our experimental results indicated that these protocols are ineffective on other *petunia* cultivars, e.g., cv. Avalanche.

Identification of suitable methods and conditions for regeneration and transformation of additional cultivars of ornamental plants is therefore needed to extend the line of future transgenic and transplastomic ornamental plant products. We have experimentally determined that explants of cultivars (i) *Petunia* cv. "Perfectunia Blue"; (ii) *Nicotiana Alata* cv. "Whisper Rose Shades"; and (iii) *Nicotiana Sylvestris* cv. "Only the Lonely" can be regenerated and transformed in tissue culture. Leaf explants of these cultivars have been derived from plants grown in sterile magenta boxes, transferred to a medium containing MS salts (Caisson), 1 mg/L BAP, 0.1 mg/L NAA, 1:1000 MS Vitamin Solution (Phytotechnology M553), 30 g/L Sucrose, 7-8 g/L Phytoagar, at pH 5.8, and cultured under a light intensity of—2000 lux and a temperature of 26-28° C. Vigorous plant regeneration started several weeks after transfer of the leaf explants to the medium. Regenerating meristems have been excised and transferred to medium containing MS salts (Caisson), 30 g/L Sucrose, 7-8 g/L Phytoagar, at pH 5.8 for rooting. Rooted plants can be transferred to soil and maintained in greenhouse or other soil conditions. Notably, this protocol did not work for a large number of other ornamental tobacco or *petunia* cultivars, including *Nicotiana* Avalon, *Nicotiana* Perfume Red, Avalanche *Petunia*, and others.

Nuclear and plastidal DNA of the regenerating cultivars can transformed via methods known in the art (e.g., *Agrobacterium*-mediated or biolistic transformation), and plants can be regenerated using the above described method. It was found that 500 mg/L of spectinomycin is particularly effective in regenerating transplastomic plants of these cultivars. One skilled in the art can appreciate that minor variations in the selective agent or regeneration medium composition will yield the same result and the present invention encompasses all such variations.

In another embodiment, the present invention relates to certain plant chloroplast sequences useful for targeting integration of transgenes into chloroplast genomes. It is beneficial to know the exact sequence of the region of the chloroplast genome where a transgene of interest can be integrated, to be used as targeting sequences in the plastid transformation vector. Homologous recombination sequences derived from tobacco are known in the art, and those are frequently used as targeting sequences in transformation vectors to generate transplastomic tobacco plants. However, when these sequences are used to generate transplastomic plants of other species (e.g., tomato or *petunia*), transformation efficiency is dramatically reduced. Further, it is well known in the art that the highest plastid transformation efficiency is achieved when the targeting sequences have full or close to 100% homology to the transformed plastidal genome.

We have therefore sequenced and identified regions of the chloroplast genome of poinsettia (SEQ ID NO:3), rose (SEQ ID NO:4), and *petunia* (SEQ ID NO:5) suitable for targeting of transgenes. These sequences can be used as homologous recombination targeting sequences within chloroplast transformation vectors for the transformation of poinsettia, rose, or *petunia*, respectively, and to integrate a variety of transgenes including, but not limited to, the LUX operon, into plastidal genomes of these commercially important ornamental species.

4.2.5 Altering the Intensity and Qualitative Properties of the Light Emitted by ALPS Enhancing Light Emission by ALPS A potential limitation of the applicability of LUX operon-based technologies, particularly in plants, is low levels of light emission in plants expressing naturally occurring LUX genes.

This problem has been solved by providing several means of enhancing light emission, which is instrumental in providing useful, highly autoluminescent phytosensor (ALPS) plants.

The present invention encompasses the use of novel artificial DNA sequences, i.e., SEQ ID NOs:6-13 and 16-17, shown in the section entitled "Nucleotide and Amino Acid Sequences of the Invention", variously encoding for LUX and other polypeptides, useful in enhancing autoluminescence in plants. These include sequences comprising specific mutations in the LuxC and LuxE genes that are highly effective in enhancing light emission in an organism, such as a bacterium or plant, containing these genes in a mutated LUX operon. Thus, these sequences are useful in all of the plant cells, plants, expression cassettes, vectors, methods, etc., disclosed and claimed herein that employ LUX operon sequences, and the terms "LUX", "LUX gene", "LUX operon", and the like as used herein encompass the use not only of naturally occurring LUX operon gene sequences, but the following novel artificial sequences as well.

These novel artificial DNA sequences are as follows:
SEQ ID NO:6: artificial Lux A nucleotide sequence;
SEQ ID NO:7: artificial Lux B nucleotide sequence;
SEQ ID NO:8: artificial Lux C nucleotide sequence, incorporating Ala→Gly mutation at amino acid position 389;
SEQ ID NO:9: artificial Lux D nucleotide sequence;
SEQ ID NO:10: artificial Lux E nucleotide sequence, incorporating Gln→Glu mutation at amino acid position 167;
SEQ ID NO:11: artificial Lux G nucleotide sequence;
SEQ ID NO:12: artificial *E. coli* Fre nucleotide sequence;
SEQ ID NO:13: artificial *V. fischeri* Yellow Fluorescent Protein nucleotide sequence;
SEQ ID NO:14: amino acid sequence of wild-type *Photobacterium leiognathi* LuxC protein;
SEQ ID NO:15: amino acid sequence of wild-type *Photobacterium leiognathi* LuxE protein;
SEQ ID NO:16: artificial Lux C nucleotide sequence without Ala→Gly mutation at amino acid position 389. Compare to SEQ ID NO:8;
SEQ ID NO:17: artificial Lux E nucleotide sequence without Gln→Glu mutation at amino acid position 167. Compare to SEQ ID NO:10.

Although not listed above, the present invention also encompasses the amino acid sequences of the proteins encoded by the nucleotide sequences listed. Such amino acid sequences can be deduced by, for example, by conventional translation known in the art.

More particularly, the present invention employs:

1. A nucleic acid construct, comprising the nucleotide sequences shown in SEQ ID NOs:6-10, operably linked for expression.

2. A nucleic acid construct, comprising the nucleotide sequences shown in SEQ ID NOs:6-11, operably linked for expression.

3. The nucleic acid construct of 1 or 2, further comprising, operably linked for expression, the nucleotide sequence shown in SEQ ID NO:12.

4. The nucleic acid construct of any one of 1-3, further comprising, operably linked for expression, the nucleotide sequence shown in SEQ ID NO:13.

5. The nucleic acid construct of any one of 1-4, which is an expression cassette.

6. An expression vector, comprising the expression cassette of 5.

The novel mutations in the structural LUX genes C (encoding an Ala→Gly mutation at amino acid position 389 (SEQ ID NO: 8)) and E (encoding a Gln→Glu mutation at amino acid position 167 (SEQ ID NO:10)) greatly enhance light emission of the LUX operon.

Artificial sequences SEQ ID NOs:12 and 13, encoding FRE and YFP proteins, respectively, are designed to further improve light output and change the emitted light color, respectively, of the autoluminescent plants encompassed by the present invention.

These nucleic acid constructs, expression cassettes, and vectors can be used to enhance autoluminescence in any of the plants or methods of the present invention.

As indicated above, preferred combinations of the artificial sequences disclosed herein include, but are not limited to: SEQ ID NOs:6-10 in combination; SEQ ID NOs:6-11 in combination; or further, combination of SEQ ID NOs:6-10 in combination or SEQ ID NOs:6-11 in combination, further in combination with SEQ ID NO:12; and further, such foregoing combinations, further in combination with SEQ ID NO:13. In each of these cases, the nucleotide sequences are operably linked for expression, and are expressed.

One skilled in the art will recognize that the individual sequences disclosed herein can be used in combination, as indicated above, in any order, and are independent of one another.

As used herein, the phrase "operably linked for expression" and the like encompasses nucleic acid sequences linked in the 5' to 3' direction in such a way as to facilitate expression of an included nucleotide coding sequence.

Altering the Qualitative Properties of Light Emitted by ALPS

The wavelength, and therefore the color, of the ALPS emitted light can be modified. The color of the light emitted by plant-expressed luciferase can be changed and modified by either of the two following exemplary approaches: (i) change in luciferase properties using directed evolution and protein engineering, as is known in the art to change enzymatic properties of different luciferases, or (ii) coupling expression with an appropriate chromophore or fluorescent protein. For example, Enhanced Green Fluorescent Protein (EGFP) has an excitation peak at approx. 490 nm, and an emission peak at about 510 nm. Co-expression of the bacterial luciferase (emitting at approx. 490 nm) with EGFP can facilitate a shift of the luminescence peak, e.g., the EGFP will be excited by luciferase emitted light and the final plant glow will be at 510 nm. Another example is the LuxY-encoded Yellow Fluorescence Protein (YFP) from certain *V. fischeri*. The YFP causes a shift in the luminescence of bacterial luciferase from approx. 490 nm to a higher wavelength, resulting in the emission of a yellow, rather than a blue-green, light.

As noted above, artificial sequences SEQ ID NOs:12 and 13, encoding FRE and YFP proteins, respectively, further improve light output and change the emitted light color, respectively, of the autoluminescent plants encompassed by the present invention.

In one embodiment, the light output improving (e.g., FRE) or color altering (e.g., YFP) genes can be expressed from either the chloroplast genome, or alternatively from the nuclear genome and targeted into chloroplasts using appropriate plastid or chloroplast targeting sequences.

In yet another embodiment, the same ALPS can be made to emit different wavelengths of light in response to different stimuli. In yet another embodiment, different ALPS can be made to emit different wavelengths of light in response to the same or different stimuli. The present invention encompasses all such possible combinations, which clearly have a variety of different practical utilities.

4.2.6. Self-Enhancing Transgene Expression Loops

Certain methods to enhance autoluminescence using a variety of co-factors, directed evolution/mutagenesis, and other methods have been described previously by Krichevsky in Patent applications PCT/US2008/009310, U.S. 60/953, 337, and PCT/US10/25366. Here, we describe yet another novel approach to enhance gene expression—and in particular expression of genes involved in autoluminescence—using a self-enhancing transgene expression loop.

In one embodiment, this method comprises an expression cassette comprising an inducible promoter, placed upstream of a transgene, the expression of which needs to be enhanced, followed by a polymerase or a transcription factor that activates the inducible promoter (FIG. 7). An example of such a promoter/inducer pair is the T7 promoter and T7 RNA polymerase (T7RNAP). The initial levels of T7RNAP can be induced by an upstream transcription of the expression cassette integrated within the host genome. For example, transcription of the expression cassette integrated into the TrnI/TrnA region of a chloroplast genome can be induced by the read-through transcription from the upstream native Prrn promoter. Once initial copies of the T7RNAP polypeptide are produced, they bind to the T7 promoter and transcribe the expression cassette. Additional T7RNAP copies produced enhance the transcription of the expression cassette even further, thus forming a self-enhancing loop, and increasing expression of the transgene of interest.

One skilled in the art will appreciate that multiple variants of the self-enhancing transgene expression loop can be contemplated, and these all are encompassed by the present invention. In one example (FIG. 7B), when overexpression of a transgene may be lethal, an operator sequence (Op) might be placed before the T7RNAP to disable loop activity until the desired time. Similarly, the operator sequence can be placed before the T7 promoter. In another example (FIG. 7B), instead of relying on native upstream transcription, an active promoter (such as Prrn) can be immediately upstream to T7p to initiate production of initial T7RNAP. In yet another example (FIG. 7C), the T7RNAP can be placed upstream to the T7 promoter.

Although this aspect of the invention is illustrated in conjunction with specific embodiments, it is evident that many alternatives, modifications, and variations will be apparent to those skilled in the art, which are all encompassed by the present invention.

4.3. Description of Certain Invention Elements

Although the invention is demonstrated by specific examples provided herein, including descriptions of certain elements that may or may not be used in the creation of autoluminescent phytosenor plants and methods for monitoring thereof, it is evident that many alternatives, modifications, and variations will be apparent to those skilled in the art. Exemplary alternatives described herein are intended to be encompassed by the appended claims.

4.3.1 Plants

The term "plant" is used broadly herein to refer to a eukaryotic organism containing a plastid, and being at any stage of development. The term "plant" as used herein refers to a whole plant or a part of a plant (e.g., a plant cutting, a plant cell, a plant cell culture, a plant organ, a plant seed, and a plantlet), a seed, a cell- or a tissue-culture derived from a plant, plant organ (e.g., embryos, pollen, ovules, seeds, leaves, flowers, branches, fruit, kernels, ears, cobs, husks, stalks, roots, root tips, anthers, etc.). The term "plant" includes any monocot or dicot. The terms "transgenic," "transformed," and "transfected" as used herein include any cell, cell line, callus, tissue, plant tissue, or plant into which a nucleic acid heterologous to the host cell has been introduced.

Any plant may be used in the practice of the present invention. For example, *Nicotiana tabacum* (tobacco) can be used, as it is frequently employed as a model organism in plant research, and a large amount of data regarding its biology has been accumulated. Obviously, also of particular importance are commercial agronomic and horticultural food and ornamental crops, including soy, corn, and cotton, and high-value, as well as non-food crops such as oilseed crops that produce seeds or fruit with a high oil content, e.g., greater than about 10%. Exemplary oil seed crops or oil crop plants include, for example, plants of the genus *Camelina*, coconut, cotton, peanut, rapeseed (canola), safflower, sesame, soybean, wheat, flax, sunflower, olive, corn, palm, sugarcane, castor bean, switchgrass, *Miscanthus*, and *Jatropha*.

A plant cell typically contains a "plastid," which refers to an organelle with its own genetic machinery in a plant cell. Examples of a plastid include chloroplasts, chromoplasts, etioplasts, gerontoplasts, leucoplasts, proplastids, amyloplasts, etc. The plastids of higher plants are an attractive target for genetic engineering. Plant plastids are major biosynthetic centers that, in addition to photosynthesis, may be responsible for production of important compounds such as amino acids, complex carbohydrates, fatty acids, and pigments. Plastids are derived from a common precursor known as a proplastid, and thus the plastids present in a given plant species all have the same genetic content. Plant cells may contain anywhere between 500-10,000 copies of a 120-160 kilobase circular plastidal genome, and can therefore be engineered to contain multiple copies of a particular gene of interest, integrated within the aforementioned plastidal genome, which potentially can result in very high levels of transgene expression. In addition, plastids of most plants are maternally inherited. Consequently, unlike transgenes expressed in the cell nucleus, heterologous genes expressed in plastids are not pollen disseminated. Thus, a trait introduced into a plant plastid will not be transmitted by pollen to wild-type relatives, thereby preventing undesired transgene escape.

4.3.2. Vectors

The term "vector" as used herein refers to a vehicle used for introduction of a nucleotide sequence into a host. A vector may be a plasmid, cosmid, phage, transposon, virus, or any other suitable vehicle known in the art. Preferably, the vector is a plasmid. A vector may include regulatory sequences useful for expression of a gene product in a host including, but not limited to, a promoter, ribosomal binding site, and termination sequences.

In one embodiment, for the transformation of nuclear host DNA, the vector is a binary vector or another type of nucleus transforming vector. A "binary vector" refers to a vector that includes a modified T-region from Ti plasmid, which allows replication in E. coli and in Agrobacterium cells, and usually includes selection marker genes. Multiple binary and other plant nucleus transformation vectors are known in the art.

In another embodiment, the vector is a plastid (chloroplast) transformation vector. Typically, a transgene expression cassette in a chloroplast transformation vector is flanked by a "homologous recombination site," which is a DNA region that is homologous to a region of the genome of a plastid. The homologous recombination sites (HRs) enable site-specific integration of a transgene expression cassette into a plastidal genome by the process of homologous recombination. Homologous recombination is a process that naturally occurs in plastids and differs from random transgene integration into the plant nuclear genome. Multiple plastid transformation vectors are known in the art. Similarly, mitochondrial transformation vectors are encompassed within the scope of this invention.

Heterologous nucleotide sequences can be used in the vectors, and include functional elements, which influence the generation, multiplication, function, use, or value of the heterologous nucleotide sequence or vector used within the scope of the present invention. Examples of functional elements include replication origins (ORI), which make possible an amplification of the heterologous nucleotide sequence or vector according to the invention in, for example, E. coli or in plastids; multiple cloning sites (MCSs), which permit and facilitate the insertion of one or more nucleic acid sequences; homologous recombination sites, allowing stable recombination of transgenes into plastid genomes; and border sequences, which make possible Agrobacterium-mediated transfer of the heterologous nucleotide sequence or vector into plant cells for the transfer and integration into the plant genome, such as, for example, the right or left border of the T-DNA or the vir region, and transcriptional and translational enhancers. Further additional sequences optionally include RNA processing signals, e.g., introns, which can be positioned upstream or downstream, or within a polypeptide-encoding sequence in the heterologous nucleotide sequence. Intron sequences are known in the art to aid in the expression of heterologous nucleotide sequences in plant cells.

4.3.3. Promoters and Terminators

The heterologous nucleotide sequence or vector described herein can include regulatory sequences useful for expression of a gene product in a host, such as a promoter. A promoter drives expression of an operably linked nucleotide sequence. The term "operably linked" as used herein refers to linkage of a promoter to a nucleotide sequence such that the promoter mediates transcription of the nucleotide sequence. A "coding sequence" refers to a nucleotide sequence that encodes a specific peptide, polypeptide, or protein amino acid sequence. A promoter is typically located upstream (5') to a coding sequence.

A wide variety of promoters is known in the art and can be used to facilitate expression of a gene in the heterologous nucleotide sequence. Examples of promoters include constitutive promoters, plant tissue-specific promoters, plant development-specific promoters, inducible promoters, circadian rhythm promoters, viral promoters, male germline-specific promoters, female germline-specific promoters, flower-specific promoters, and vegetative shoot apical meristem-specific promoters. Inducible promoters that respond to various internal and/or external stimuli affecting plants are particularly useful in the ALPS plants and monitoring systems disclosed herein.

A "constitutive" promoter refers to a promoter that causes a gene to be expressed in all cell types at all times. An example of a constitutive plastid promoter is a 16S rRNA gene promoter (Prrn). Examples of nuclear genomic constitutive plant promoters include the cauliflower mosaic virus (CaMV) 35S promoter or native plant ubiquitin promoter, which confer constitutive, high-level expression in most plant cells; the nopaline synthase promoter; the octopine synthase promoter; cauliflower mosaic virus 19S promoter; rice actin 1 promoter; mannopine synthase promoter; and a histone or an actin promoter. Further suitable constitutive promoters include the Rubisco small subunit (SSU) promoter, leguminB promoter, TR dual promoter, ubiquitin promoter, and Super promoter. Different heterologous nucleotide sequences or vectors can contain different promoters to prevent gene silencing when several consecutive genes on a chromosome are expressed from the same promoter.

4.3.4. Inducible Promoters

An "inducible" promoter refers to a promoter that is regulated in response to a stress, a condition, or a stimulus. Examples of inducible promoters include a tetracycline repressor system, Lac repressor system, copper-inducible system, salicylate-inducible system (such as the PR 1a system), and an alcohol-inducible system. Further examples include inducible promoters that are regulated in response to environmental, hormonal, chemical, and/or developmental stress or stimuli. Such stresses or stimuli include heat (e.g., tomato hsp70 promoter or hsp80 promoter); cold; light; drought (e.g., Arabidopsis rd29A promoter); hormones, such as abscisic acid; chemicals, such as methyl jasmonate, salicylic acid; increased salinity; pathogens (e.g., promoter of the PRP1 gene); heavy metals (e.g., heavy metal-inducible metallothionein I promoter and the promoter controlling expression of the tobacco gene cdiGRP; wounds (e.g., pinII promoter), and radiation.

In yet another aspect of the invention, in addition to the naturally occurring inducible promoters, an inducible promoter can be specifically designed to be responsive to a specific stimulus. For example, pathogen inducible promoters can be designed and synthetically produced (Raveendra G. M., "Designing pathogen-inducible synthetic promoters and functional validation of a new eukaryotic promoter-probe vector"; Graduate Thesis, Department of Biotechnology, College of Agriculture, Dharwad University of Agricultural Sciences, Dharwad).

The term "tissue-specific" promoter as used herein refers to a promoter that drives expression of an operably linked nucleotide sequence in a particular tissue. A tissue-specific promoter drives expression of a gene in one or more cell types in a specific organ (such as leaves, or seeds), specific tissues (such as embryo or cotyledon), or specific cell types (such as seed storage cells or leaf parenchyma). Examples include the Gentiana triflora promoter for chalcone synthase (NCBI accession AB005484), a seed-specific promoter, such as the β-conglycinin, napin, and phaseolin promoters; mature leaves-specific promoters, such as the SAG promoter from *Arabidopsis*.

Promoters responsible to the circadian rhythm cycle can also be used in the heterologous nucleotide sequence or vector. Such promoters include the native ELF3 promoter and the promoter from the chlorophyll a/b binding protein (CAB2 promoter).

Transgene expression can also be regulated by a terminator sequence. Examples and use of the terminator sequences are known in the art, and include the psbA photosystem II reaction center terminator or gene rps16 terminator for plastid-expressed genes, Cauliflower Mosaic Virus (CaMV) 35S terminator, or *Arabidopsis* Heat Shock Protein 18.2 or Ubiquitin 5 (UBQ 5) terminators for nucleus-expressed transgenes.

4.3.5. Markers and Marker Removal Systems

In addition, the heterologous nucleotide sequence or vector can include a nucleotide sequence for a selectable and/or screenable marker. A "selection marker" refers to a protein necessary for survival or growth of a transformed plant cell grown in a selective culture regimen. Typical selection markers include sequences that encode proteins, which confer resistance to selective agents, such as antibiotics, herbicides, or other toxins. Examples of selection markers include genes conferring resistance to antibiotics, such as spectinomycin, streptomycin, tetracycline, ampicillin, kanamycin, G 418, neomycin, bleomycin, hygromycin, methotrexate, dicamba, glufosinate, or glyphosate.

Various other selection markers confer a growth-related advantage to transformed cells over non-transformed cells. Examples include selection markers for β-glucuronidase (in conjunction with, for example, cytokininglucuronide), mannose-6-phosphate isomerase (in conjunction with mannose), and UDP-galactose 4-epimerase (in conjunction with, for example, galactose).

Selection markers include those that confer resistance to spectinomycin (e.g., encoded by the resistance gene, aadA), streptomycin, kanamycin, lincomycin, gentamycin, hygromycin, methotrexate, bleomycin, phleomycin, blasticidin, sulfonamide, phosphinothricin, chlorsulfuron, bromoxynil, glyphosate, 2,4-D, atrazine, 4-methyltryptophan, nitrate, S-aminoethyl-L-cysteine, lysine/threonine, aminoethyl-cysteine or betaine aldehyde. Preferably, the selection marker is functional in plastids. Preferred are the genes aadA (GeneBank NC_009838), nptII (GeneBank FM177583), BADH (GeneBank AY050316), aphA-6 (GeneBank X07753). Especially preferred selection markers are naturally occurring alleles, such as mutation in the small ribosomal RNA (rrn16) gene that confers resistance to spectinomycin, and which can be used instead of the known selection marker aadA, or selection markers with History of Safe Use, such as nptII.

After a heterologous nucleotide sequence has been introduced into a host cell, it may be advantageous to remove or delete certain sequences from the plastome or genome of the plant or cell. For example, it may be advantageous to remove a selection marker gene that has been introduced into a genome if the selection marker is no longer necessarily required after the selection phase. Methods for directed deletion of sequences are known in the art. For example, the nucleotide sequence encoding a selection marker preferably includes a homology-based excision element, such as Cre-lox and attB/attP recognition sequences, which allow removal of the selection marker genes using site-specific recombinases.

In one embodiment, the heterologous nucleotide sequence or vector includes reporter genes. Reporter genes encode readily quantifiable proteins which, via their color or enzyme activity for example, facilitate assessment of the transformation efficiency, the site or time of expression, or the identification of transgenic plants. Examples of reporter genes include green fluorescent protein (GFP), luciferase, β-Galactosidase, β-Glucuronidase (GUS), R-Locus gene product, β-Lactamase, xylE gene product, alpha-amylase, and tyrosinase.

4.3.6. Plastid Targeting Sequences

In another embodiment of the present invention, the heterologous nucleotide sequence includes a plastid targeting sequence. A "plastid targeting sequence" as used herein refers to a nucleotide sequence that encodes a polypeptide sequence, which can direct a second polypeptide to a plastid of the plant cell. Preferably, the plastid targeting sequence is a chloroplast targeting sequence.

It is known in the art that non-chloroplast proteins may be targeted to the chloroplast by use of protein fusions with a peptide encoded by a chloroplast targeting sequence. For example, luciferase genes of a heterologous nucleotide sequence can be fused with a plastid targeting sequence. When the luciferase gene is expressed, the targeting sequence is included in the translated polypeptide. The targeting sequence then directs the polypeptide into a plastid, such as a chloroplast.

Typically, the chloroplast targeting sequence encodes a polypeptide extension (called a chloroplast transit peptide (CTP) or transit peptide (TP)). The polypeptide extension is typically linked to the N-terminus of the heterologous peptide encoded by the heterologous nucleotide sequence.

Examples of a chloroplast targeting sequence include a sequence that encodes the tobacco ribulose bisphosphate carboxylase (Rubisco) small subunit (RbcS) transit peptide, *Arabidopsis thaliana* EPSPS chloroplast transit peptide, the *Petunia* EPSPS chloroplast transit peptide, and the rice rbcS gene chloroplast targeting sequence.

Further examples of a chloroplast target peptide include the small subunit (SSU) of ribulose-1,5-biphosphate carboxylase, and the light harvesting complex protein I and protein II. Incorporation of a suitable chloroplast targeting peptide has been shown to target heterologous protein sequences to chloroplasts in transgenic plants. Those skilled in the art will recognize that various chimeric constructs can be made, if needed, that utilize the functionality of a particular CTP to import a given gene product into a chloroplast.

Other CTPs that may be useful in practicing the present invention include PsRbcS-derived CTPs (*Pisum sativum* Rubisco small subunit CTP); AtRbcS CTP (*Arabidopsis thaliana* Rubisco small subunit 1A CTP; CTP1); AtShkG CTP(CTP2); AtShkGZm CTP (CTP2synthetic; codon optimized for monocot expression); PhShkG CTP (Petunia EPSPS; CTP4; codon optimized for monocot expression); TaWaxy CTP (*Triticum aestivum* granule-bound starch synthase CTP synthetic, codon optimized for corn expression): OsWaxy CTP (*Oryza sativa* starch synthase CTP); NtRbcS CTP (*Nicotiana tabacum* ribulose 1,5-bisphosphate carboxylase small subunit chloroplast transit peptide); ZmAS CTP (*Zea mays* anthranilate synthase alpha 2 subunit gene CTP); and RgAS CTP (*Ruta graveolens* anthranilate synthase CTP). Other transit peptides that may be useful include the maize cab-m7 signal sequence and the pea (*Pisum sativum*) glutathione reductase signal sequence.

4.3.7. Plant Sterility

In one aspect of the invention, ALPS or other plants described herein can be rendered sterile and incapable of reproduction. For example, the heterologous nucleotide sequence may include a sterility operon, which refers to one or more genes rendering the plant incapable of reproduction. Sterility operons and other methods to render plant sterile are known in the art.

In yet another aspect, the heterologous nucleotide sequence includes a toxin-encoding sequence operably linked to a plant-embryo specific promoter. Production of the toxin in the developing plant embryos will lead to cell death within those embryos, thus terminating their development and leaving the plant sterile.

4.3.8. Sequence Variants

The present invention further relates to variants of the nucleotide and protein sequences described herein. Variants may occur naturally, such as a natural allelic variant. Other variants include those produced by nucleotide substitutions, deletions, or additions. The substitutions, deletions, or additions may involve one or more nucleotides or amino acids. These variants may be altered in coding regions, non-coding regions, or both. Alterations in the coding regions may produce conservative or non-conservative amino acid substitutions, deletions, or additions. Preferably, the variant is a silent substitution, addition, or deletion, which does not alter the properties and activities of the protein encoded by the nucleotide sequence described herein. Conservative substitutions are also preferred.

A variant of a sequence can comprise a sequence having at least about 90% sequence identity, and more preferably at least about 95%, 96%, 97%, 98%, or 99% sequence identity, to a claimed nucleotide or amino acid sequence, and which exhibits the same or similar biological activity as the reference sequence, plus or minus about 25%, about 20%, about 15%, about 10%, about 5%, or less. For example, a variant nucleotide sequence that is at least about 95% identical to a claimed nucleotide sequence is identical to the latter sequence, except that the variant nucleotide sequence may include up to five point mutations per each 100 nucleotides of the reference nucleotide sequence described herein.

To determine percent identity of two nucleic acid sequences, the sequences are aligned for optimal comparison purposes (e.g., gaps can be introduced in one or both of a first and second nucleotide sequence for optimal alignment). For example, when aligning a first sequence to a second sequence having 10 nucleotides, at least 70%, preferably at least 80%, more preferably at least 90% of the 10 nucleotides between the first and second sequences are aligned. When a position in the first sequence is occupied by the same nucleotide as the corresponding position in the second sequence, then the molecules are identical at that position. The percent identity between the two sequences is a function of the number of identical positions shared by the sequences, taking into account the number of gaps, the length of the sequences, and the length of each gap that need to be introduced for optimal alignment of the two sequences. Algorithms known in the art, e.g., ClustalW or Lalign, can be used to determine percent identity between the two sequences.

The following examples describe various aspects of the present invention, and are merely intended to be illustrative rather than limiting of the compounds, compositions, and methods useful therein.

5.0 EXAMPLES

Example 1

Construction of Chloroplast Transformation Vectors

In one aspect of the invention, the chloroplast transformation vector has been constructed based on Bioglow's cloning vector pBGL (FIG. 8). The aadA selection marker was PCR amplified using forward 5'-GCTTCCATGGGGGAAGCG-GTGATCGCCGAAG-3' (SEQ ID NO:18) and reverse 5'-GTATGCATGCTTATTTGCCGACTACCTTGGTGATC-3' (SEQ ID NO:19) primers and cloned using NcoI/SphI into pBGL. Primers 5'-TTTCCCTCTAGAAATAATTTTGTT-TAACTTTAAGAAGGAGATATAC-CATGGGGGAAGCGGTGATCGCCGAAG-3' (SEQ ID NO:20) and 5'-CCGTTGTGGTCTCCCTATAGTGAGTCG-TATTAATTTCGCGGCGCGCCTACCGGTTTAAAC-3' (SEQ ID NO:21) were used to PCR the whole vector, followed by self-ligation of the PCR products, and introducing the phage T7 gene 10 promoter (T7g10p) into the construct. Nicotiana tabacum plastidal TpsbA terminator was cloned as a NdeI/PstI PCR fragment amplified using forward 5'-CAGT-CATATGATCCTGGCCTAGTCTATAGG-3' (SEQ ID NO:22) and reverse 5'-CTGTCTGCAGTCGAATAT-AGCTCTTCTTTCTTATTTC-3' (SEQ ID NO:23) primers. The resulting vector has been designated as pBGL-T7p (FIG. 8).

The *Photobacterium leiognathi* LUX operon has been cloned downstream of the aadA selection marker in pBGL-T7p. The operon has been PCR amplified using forward 5'-CAACGAATTCCCAAAGGAGATTACATGATTAAG-3' (SEQ ID NO:24) and reverse 5'-CGTTCCGCGGTTACG-TATAGCTAAATGCATCAG-3' (SEQ ID NO:25), and cloned using EcoRI/SacII. Optionally, the vector may contain a flavin reductase to enhance light output capacity. In one instance, *E. coli* Fre flavin reductase containing phage T7 translational leader has been PCR amplified using forward 5'-GCACCGCGGAGACCACAACGGTTTC-CCTCTAGAAATAATTTTGTTTAACTT-TAAGAAGGAGATATACCATGACAACCT-TAAGCTGTAAAG-3' (SEQ ID NO:26) and reverse 5'-CTGTGGTACCTCAGATAAATGCAAACG-CATCGCCAAAC-3' (SEQ ID NO:27) primers and cloned by three way ligation downstream of the LUX operon using SacII/KpnI. Homologous recombination (HR) sequences, used to integrate the LUX expression cassette into the plastidal genome, were cloned on the left- and right-flank sides of the cassette. The TrnI and TrnA tobacco HR sequences, known in the art, have been PCR amplified from the genome of *Nicotiana tabacum*, and cloned using AgeI/AscI and NotI/PstI, respectively, to flank the LUX expression cassette. The resulting vector, pBGL-T7p-LUX-Tobacco (FIG. 8) has been verified using restriction digest and sequencing. Representative DNA digests, as well as maps of the pBGL-T7p and pBGL-T7p-LUX-Tobacco vectors, are shown in FIGS. 8 and 9, respectively.

Example 2

Generation of Autoluminescent Plants

Plastids of any plant species can potentially be transformed by a chloroplast transformation vector carrying the LUX operon. In this particular instance, we used *Nicotiana tabacum* (tobacco) plants for demonstration purposes. Transplastomic tobacco plants have been generated according to methods known in the art. Briefly, 0.6 micron gold particles (BioRad) coated with pBGL-T7p-LUX-Tobacco vector DNA were bombarded into leaves of aseptically grown 4-6 weeks old tobacco plants using PDS-1000/He Biolistic Particle Delivery System (system settings: bombardment He pressure approx. 250 psi above rapture disk pressure, [rapture disks of 1,100 psi were used]; distance from the top of the chamber 9 cm [third slot], chamber vacuum pressure 28 in Hg). The bombarded leaves were incubated at 25-26° C. in dark for 2-3 days and dissected to 5×5 mm squares, which were placed in deep Petri dishes containing 50 ml of RMOP medium (RMOP per liter: MS salts, Caisson, cat# MSP01, according to manufacturer's instructions; 100 mg myo-inositol; 1 mg thiamine HCl; 1 mg 6-benzylamino purine; 0.1 mg 1-naphthaleneacetic acid; 30 gr sucrose; 6 g phytoblend, (Caisson), pH=5.8 adjusted with KOH), supplemented with 500 ug/ml of spectinomycin (Sigma). The Petri dishes were sealed with parafilm and cultivated under cool-white fluorescent lamps (~2,000 lux) with 16 h light/8 h dark cycle at 27° C. Transplastomic plants appeared within 4-8 weeks post bombardment. As the T7 promoter is not expressible on its own in chloroplasts, the expression aadA and the LUX operon was driven by the read-through transcription from native chloroplast genome beyond the limits of the integrated expression cassette. Indeed, transplastomic plants generated using pBGL-T7p-LUX-Tobacco were resistant to spectinomycin, and exhibited very low levels of active light emission. The plants were transferred and further aseptically maintained in magenta boxes on MSO medium (MSO per liter: MS salts, Caisson, cat#MSP01, according to manufacturer's instructions; 30 gr sucrose; 6 g phytoblend (Caisson), pH=5.8 adjusted with KOH) supplemented with 500 μg/ml of spectinomycin (Sigma) under cool-white fluorescent lamps (1,900-2,000 lux) with 16 h light/8 h dark cycle at 26° C. Some of the plants have been transferred to soil in the greenhouse for propagation.

Example 3

Generation of Autoluminescnet Phytosensor (ALPS) Plants

Transplastomic plants produced using pBGL-T7p-LUX-Tobacco as described in Example 2 were used to generate ALPS plants, where T7 RNA Polymerase (T7RNAP) is expressed in the nucleus and the resulting polypeptide is transported to the chloroplast by N-terminal fusion of a transit peptide to activate LUX operon expression. T7RNAP expression can be driven by any promoter in the nucleus. For this example, we chose the drought inducible rd29A of *Arabidopsis* and constitutive NOS promoters (with NOS-driven T7RNAP plants used as positive control), and binary vectors carrying rd29A-T7RNAP and NOS-T7RNAP have been designated as pDI-rd29A and pDI-PC (Positive Control), respectively. The base vector contained the following expression cassette: AscI-NOS promoter-MCS (SalI-BglII-Sad-EcoRI-KpnI-HindIII-BamHI-PstI-StuI)-NOS terminator. Tobacco ribulose 1,5-bisphosphate carboxylase transit peptide (Rbc-STP) was PCR amplified using primers 5'-CTTCAA-GATCTCCATGGCTTCCTCAGTTCTTTCCTC-3' (SEQ ID NO:28) and 5'-GTAGGGAATTCGCATTGCACTCTTC-CGCCGTTG-3' (SEQ ID NO:29) and cloned as a BglII/EcoRI fragment, followed by cloning of T7RNAP as an EcoRI/HindIII PCR fragment, resulting in translationally fused T7RNAP and transit peptide. The resulting vector has been designated as pDI-PC (Positive Control). Then, the NOS promoter was replaced using AscI/NcoI by *Arabidiopsis* rd29A promoter, amplified using primers 5'-CATCAG-GCGCGCCTCTATCATTTAATCTGAGTCC-3' (SEQ ID NO:30) and 5'-CTGATTCCATGGTTTCCAAA-GATTTTTTTCTTTCCAATAG-3' (SEQ ID NO:31) and *Arabidopsis* genomic DNA as a template, and the resulting vectors were designated as pDI-rd29A. pDI-PC and pDI-rd29A have been used to generate transgenic plants using standard transformation methods on a background of the transplastomic line described in Example 2 (made using pBGL-T7p-LUX-Tobacco).

Example 4

Monitoring of Autoluminescent Phytosensor (ALPS) Plants

Monitoring of light emission can be accomplished via a plethora of methods and sensors as discussed herein. In one instance, and to demonstrate the feasibility of the invention, FIG. 10 shows detection of light emission from pDI-PC transformed as compared to pDI-rd29A transformed lines. The images were taken using a BioRad ChemiDoc XRS Molecular Imager when the plants were grown in tissue culture magenta boxes (inverse images shown for light detection). In conditions of 100% humidity within the magenta boxes, the *Arabidopsis* rd29A drought-inducible promoter is not expected to be active, and thus the transgenic line made using pDI-rd29A does not emit light. On the other hand, the line generated using pDI-PC exhibits constitutive T7RNAP expression, and thus emits light continuously even under high humidity conditions, as shown in FIG. 10.

This example demonstrates that light emission of ALPS phytosensors can be differentially controlled by specific promoters, according to the activity of a promoter under a given set of conditions. This principle can be further employed to generate a variety of ALPS phytosensors for the abundance and variety of different conditions and stimuli described herein.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A transplastomic plant cell containing a LUX operon comprising LUX genes integrated within a plastidal genome therein,
   wherein any or all of said LUX genes are separated by an intercistronic expression element (IEE) operably linked thereto,
   wherein expression of said LUX genes is enhanced by a heterologous translational leader sequence operably linked to one or more of said LUX genes,
   wherein said heterologous translational leader sequence is a T7g10 leader sequence, and
   wherein said transplastomic plant cell is selected from the group consisting of a species of *petunia* and a species of *Nicotiana*.

2. A method of producing an autoluminescent plant comprising: introducing into a plant cell plastid an expression cassette containing a LUX operon comprising LUX genes,
   wherein any or all of said LUX genes are separated by an intercistronic expression element (IEE) operably linked thereto,
   wherein expression of said LUX genes is enhanced by a heterologous translational leader sequence operably linked to one or more of said LUX genes,
   wherein said heterologous translational leader sequence is a T7g10 leader sequence,
   wherein said plant cell plastid is regenerated into a mature transplastomic plant, and
   wherein said transplastomic plant is selected from the group consisting of a species of *petunia* and a species of *Nicotiana*.

3. A transplastomic plant of claim 2, wherein the transplastomic plant is chosen from *Petunia* cv. "Perfectunia Blue", *Nicotiana* Alata cv. "Whisper Rose Shades", or *Nicotiana* Sylvestris cv. "Only the Lonely".

* * * * *